United States Patent
Kenney

(10) Patent No.: US 7,207,960 B2
(45) Date of Patent: Apr. 24, 2007

(54) ORTHOTIC DEVICE

(75) Inventor: John P. Kenney, Laguna Hills, CA (US)

(73) Assignee: NeuroFlex Orthotics, Inc., Laguna Hills, CA (US)

( * ) Notice: Subject to any disclaimer, the term of this patent is extended or adjusted under 35 U.S.C. 154(b) by 388 days.

(21) Appl. No.: 11/076,566

(22) Filed: Mar. 9, 2005

(65) Prior Publication Data

US 2005/0209541 A1    Sep. 22, 2005

Related U.S. Application Data

(60) Provisional application No. 60/554,035, filed on Mar. 17, 2004.

(51) Int. Cl.
*A61F 5/00* (2006.01)

(52) U.S. Cl. .............. 602/5; 602/16; 602/20; 602/23; 602/62; 128/878; 128/882

(58) Field of Classification Search .............. 602/5, 602/16, 20, 21, 23, 24, 25, 26, 27, 62, 63, 602/64, 65, 66; 128/845, 869, 878, 881, 128/882

See application file for complete search history.

(56) References Cited

U.S. PATENT DOCUMENTS

| | | | | |
|---|---|---|---|---|
| 4,643,176 A | * | 2/1987 | Mason et al. | 602/16 |
| 4,665,905 A | * | 5/1987 | Brown | 602/16 |
| 4,982,732 A | * | 1/1991 | Morris | 602/16 |
| 5,328,446 A | * | 7/1994 | Bunnell et al. | 602/16 |
| 5,782,784 A | | 7/1998 | Wassermann | |
| 5,817,040 A | * | 10/1998 | Hess et al. | 602/16 |
| 5,891,068 A | | 4/1999 | Kenney | |
| 6,074,355 A | * | 6/2000 | Bartlett | 602/16 |
| 6,383,156 B1 | * | 5/2002 | Enzerink et al. | 602/23 |
| 6,413,232 B1 | * | 7/2002 | Townsend et al. | 602/16 |
| 6,770,045 B2 | * | 8/2004 | Naft et al. | 602/26 |

OTHER PUBLICATIONS

Davide Leone, "Investigation of Stiffness Characteristics of Three Low Load Passive Stretch Devices", University of Louisville Mechanical Engineering, Aug. 24, 2000-May 1, 2001.

Thomas W. Overberg III, Investigation of Stiffness Characteristics of a Passive Stretch Device, University of Louisville, Mechanical Engineering, Aug. 24-Dec. 18, 1998.

\* cited by examiner

*Primary Examiner*—Fadi H. Dahbour
(74) *Attorney, Agent, or Firm*—Walter A. Hackler

(57) ABSTRACT

An orthotic device for restoring range of motion to a patient's limb, includes a first device cuff configured for attaching the device to an upper region of a patient's limb above a limb joint, a second device cuff configured for attaching the device to a lower region of the patient's limb below the limb joint, and a spring attached between the first and second cuffs for bending in a manner counteracting muscle contraction of the limb to which the device is attached, the spring having spring characteristics whereby a counteracting spring force of the spring increases during an initial flexing of the spring through a first angle range, then remains peaked during a subsequent flexing of the spring through a second angle range and finally decreases with a subsequent flexing of the spring through a third angle range.

10 Claims, 19 Drawing Sheets

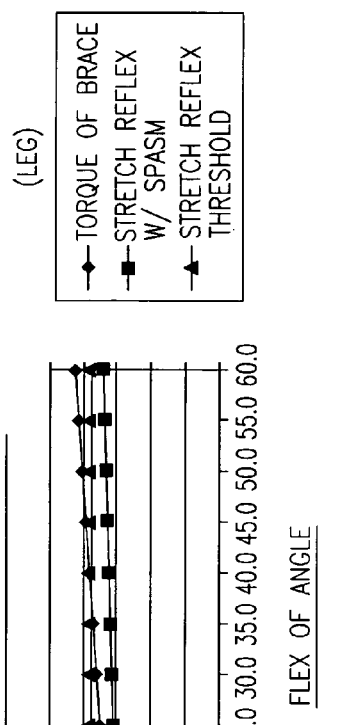

DYNAMIC POSITIVE LINEAR FOR THE LEG

| FLEX ANGLE | (AVERAGE TENSION SETTING) BRACE TORQUE (IN.LBS.) | (LEG) STRETCH REFLEX THRESHOLD | THEORETICAL (LEG) STRETCH REFLEX W/SPASM |
|---|---|---|---|
| 15.0 | 160.0 | 180 | 150.0 |
| 20.0 | 165.0 | 180 | 152.5 |
| 25.0 | 170.0 | 180 | 155.0 |
| 30.0 | 175.0 | 180 | 157.5 |
| 35.0 | 180.0 | 180 | 160.0 |
| 40.0 | 185.0 | 180 | 162.5 |
| 45.0 | 190.0 | 180 | 165.0 |
| 50.0 | 195.0 | 180 | 167.5 |
| 55.0 | 200.0 | 180 | 170.0 |
| 60.0 | 205.0 | 180 | 172.5 |

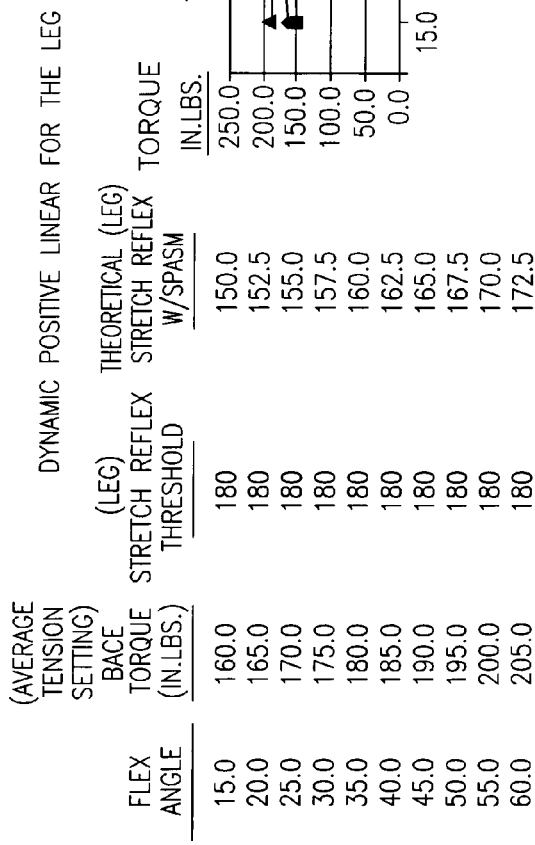

Fig.8 (PRIOR ART)

TORQUE VS ANGLE OF FLEXING (LEG)

— TORQUE OF BRACE
— STRETCH REFLEX W/ SPASM
— STRETCH REFLEX THRESHOLD

DYNAMIC POSITIVE LINEAR FOR THE ARM

| FLEX ANGLE | (AVERAGE TENSION SETTING) BRACE TORQUE (IN.LBS.) | (ARM) STRETCH REFLEX THRESHOLD | THEORETICAL (ARM) STRETCH REFLEX W/SPASM |
|---|---|---|---|
| 15.0 | 100.0 | 120 | 90.0 |
| 20.0 | 105.0 | 120 | 92.5 |
| 25.0 | 110.0 | 120 | 95.0 |
| 30.0 | 115.0 | 120 | 97.5 |
| 35.0 | 120.0 | 120 | 100.0 |
| 40.0 | 125.0 | 120 | 102.5 |
| 45.0 | 130.0 | 120 | 105.0 |
| 50.0 | 135.0 | 120 | 107.5 |
| 55.0 | 140.0 | 120 | 110.0 |
| 60.0 | 145.0 | 120 | 112.5 |

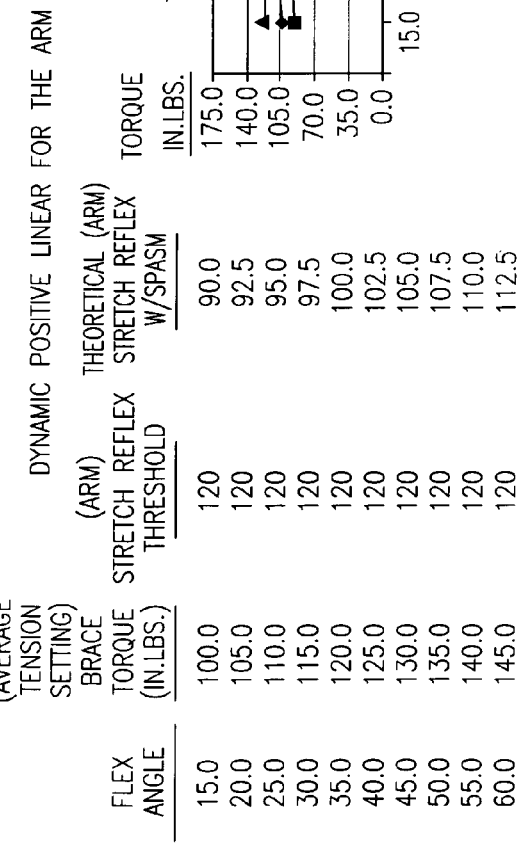

Fig.9 (PRIOR ART)

TORQUE VS ANGLE OF FLEXING (ARM)

— TORQUE OF BRACE
— STRETCH REFLEX W/ SPASM
— STRETCH REFLEX THRESHOLD

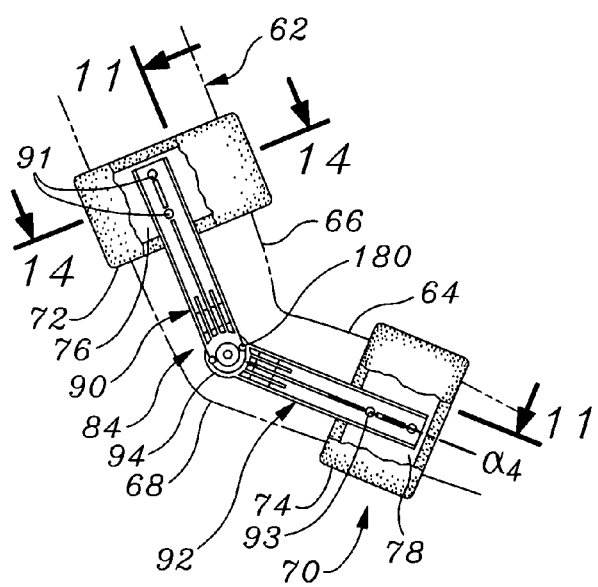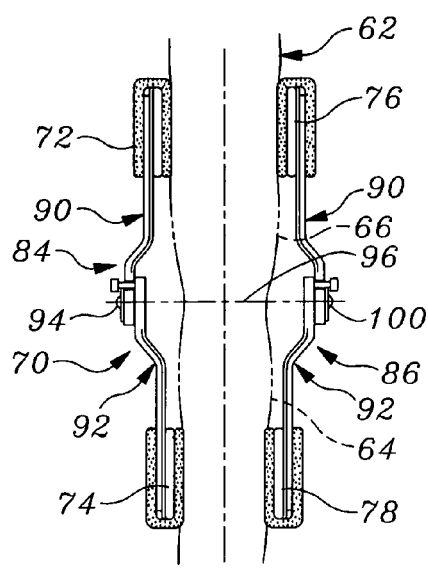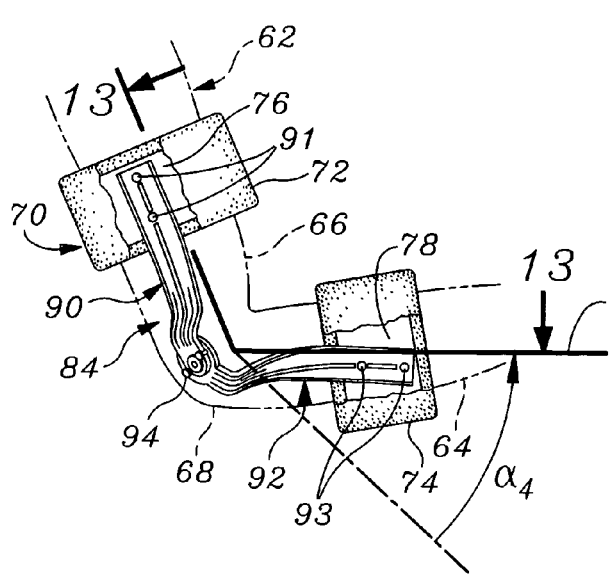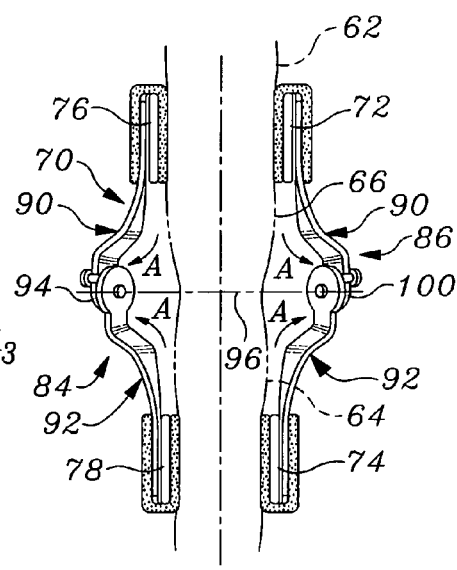

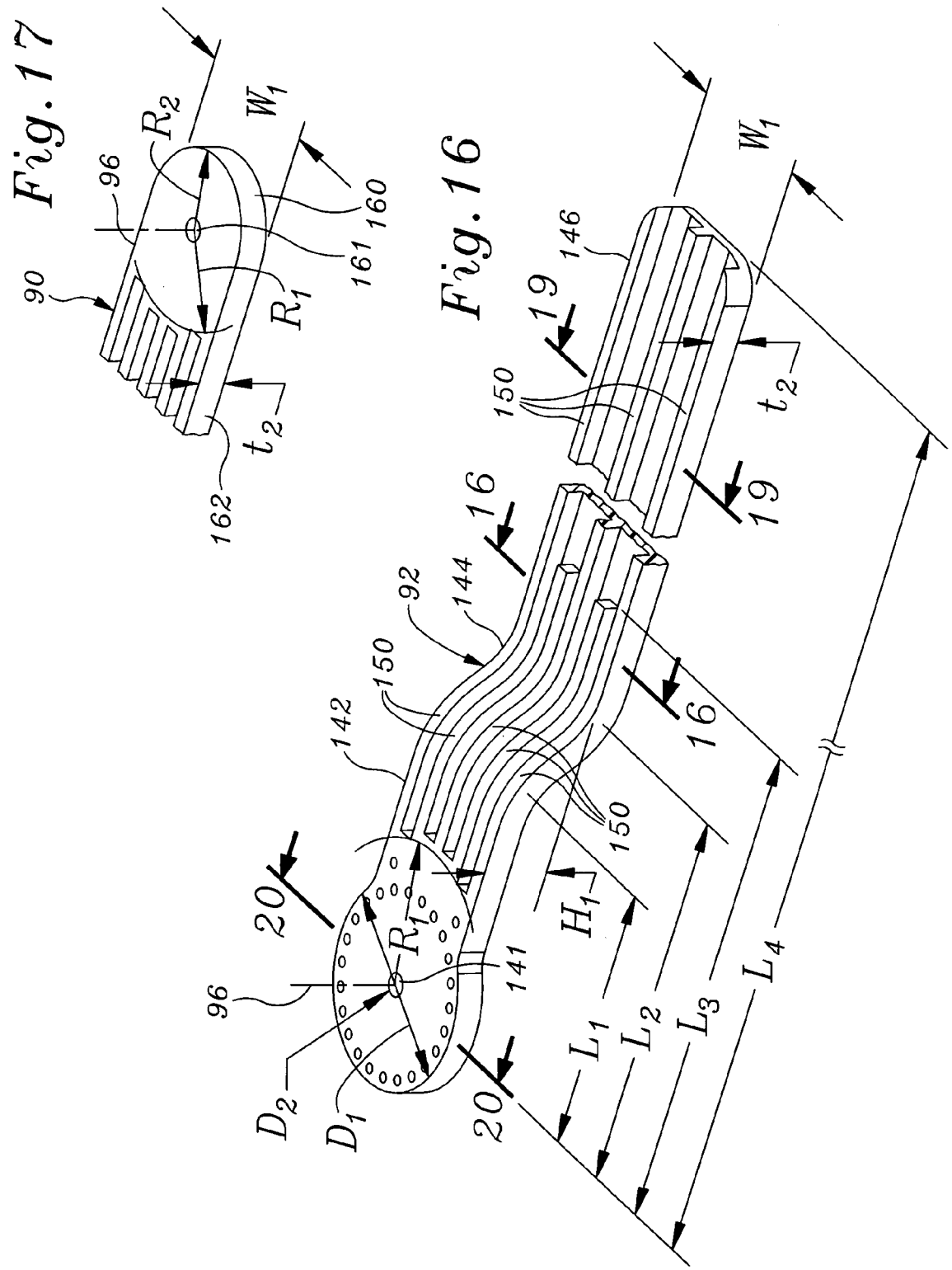

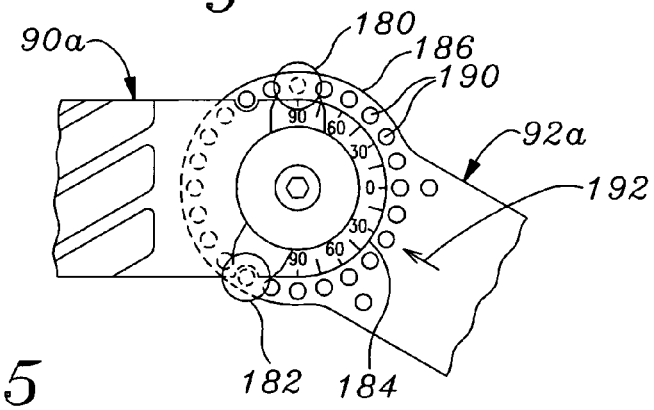
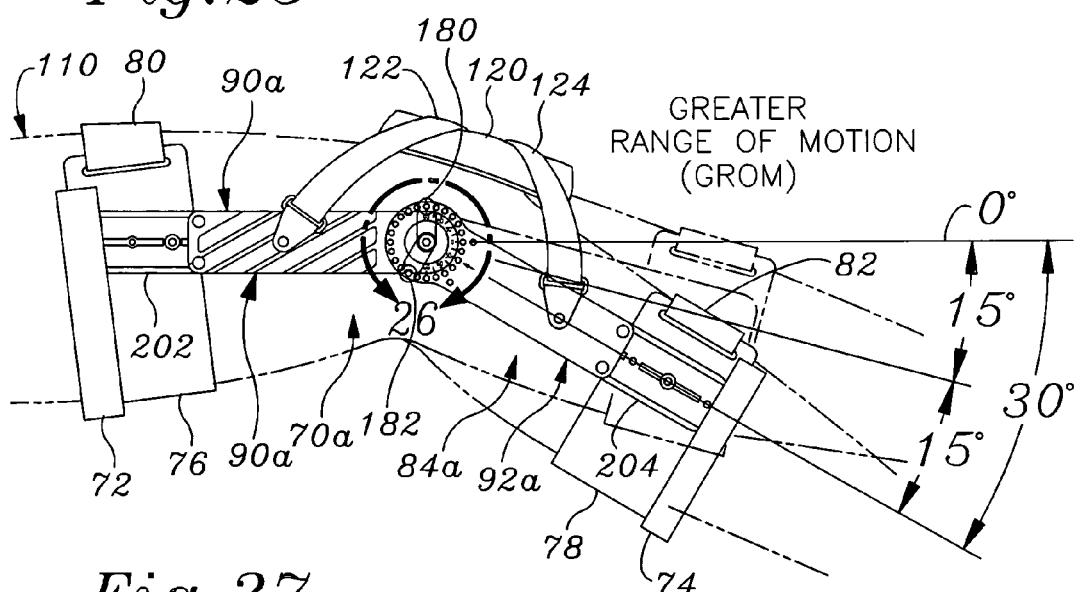
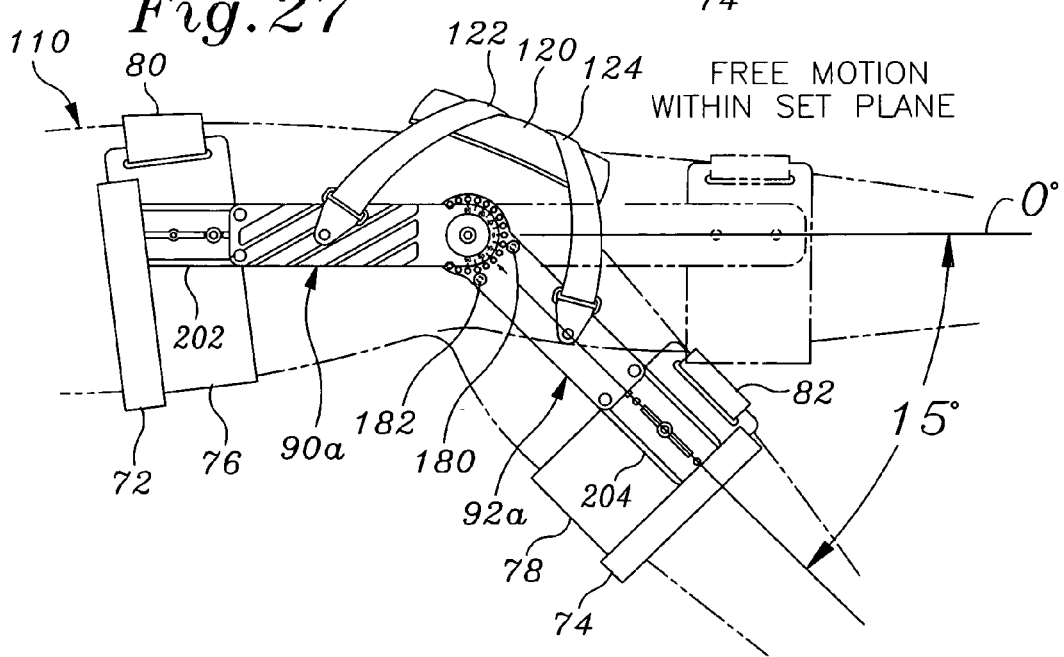

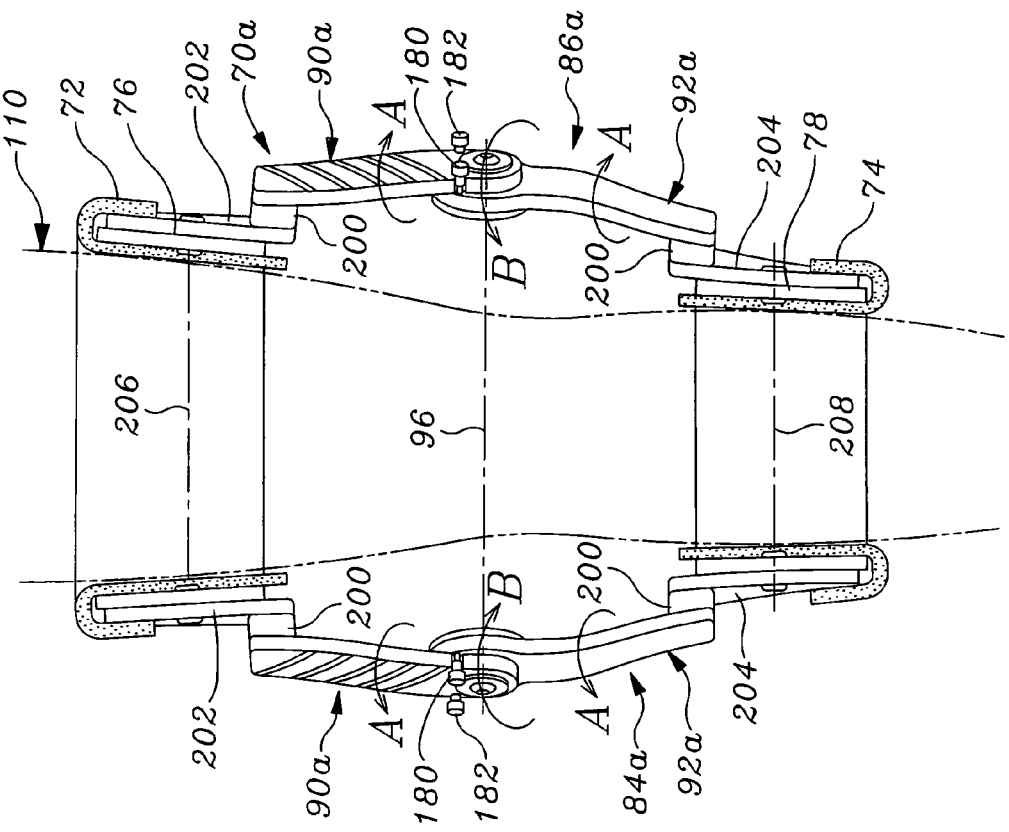
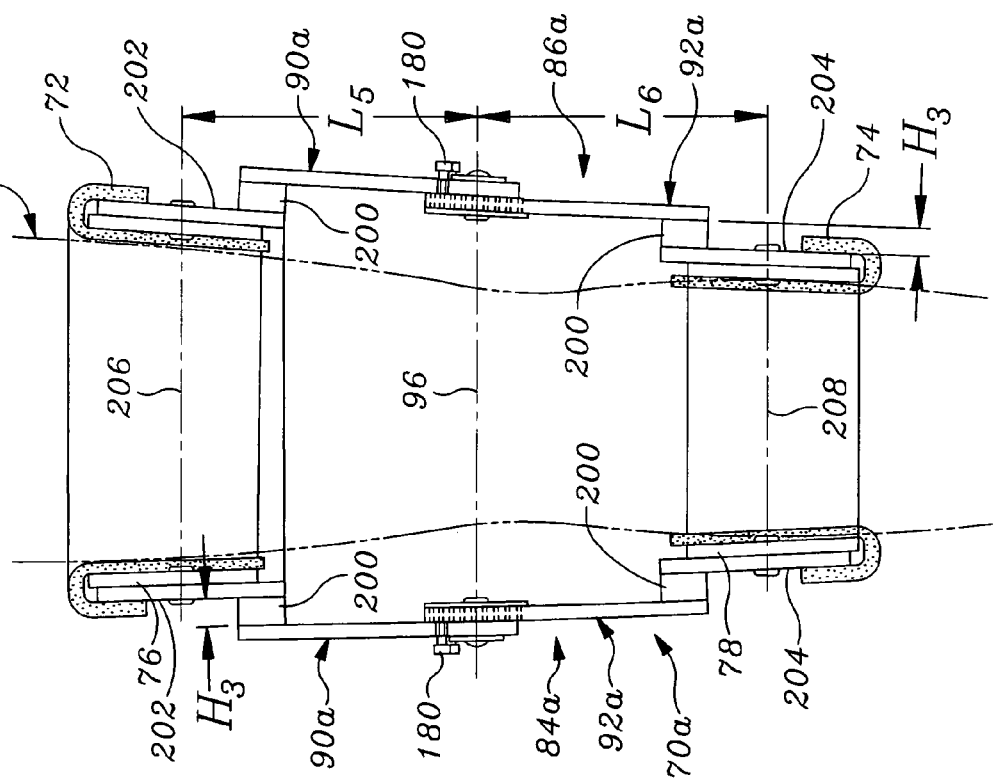

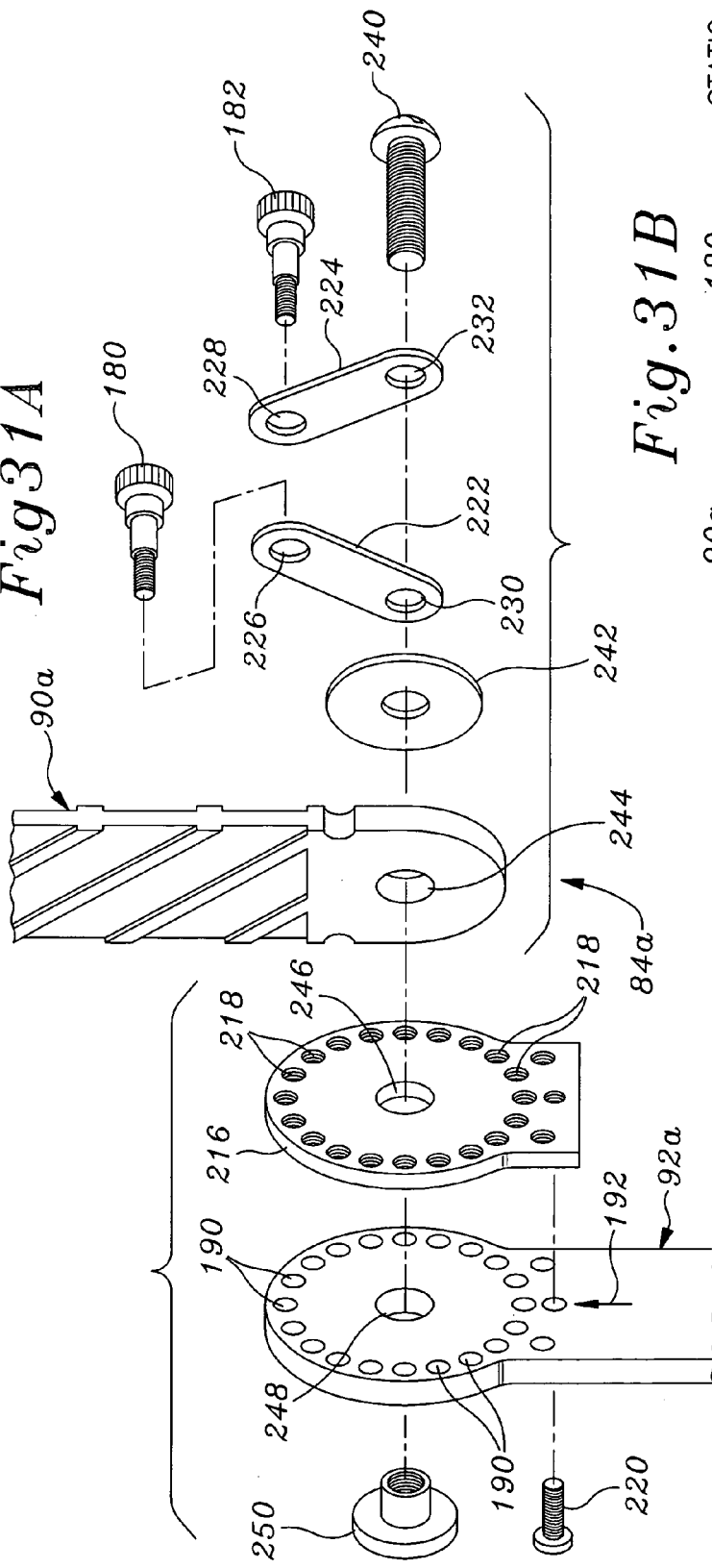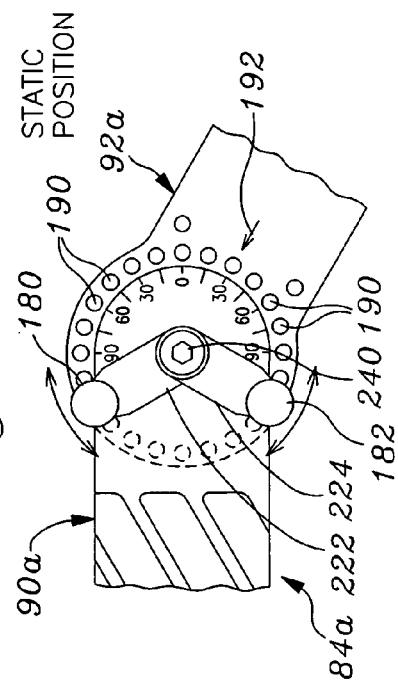

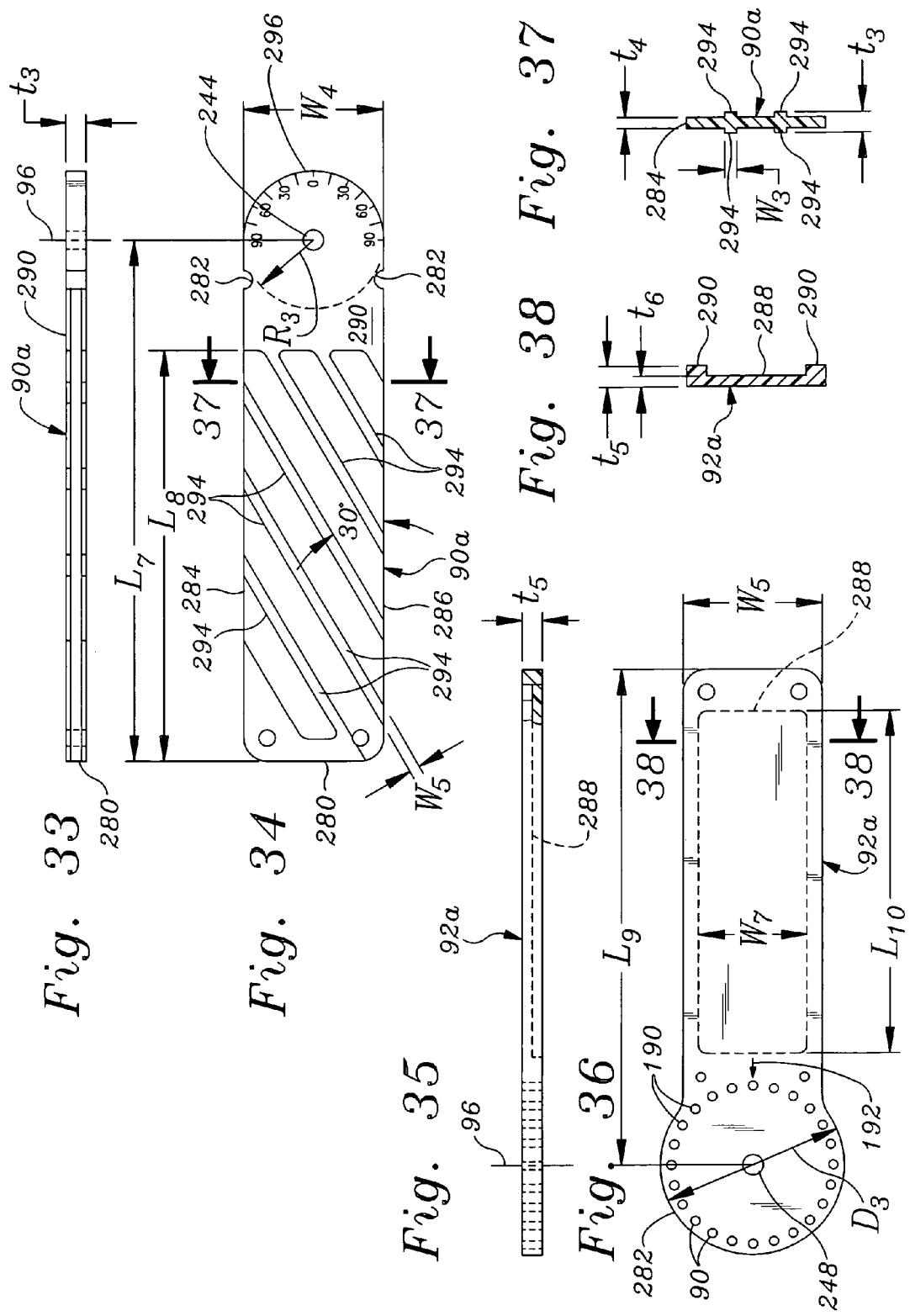

ORTHOTIC DEVICE

The present application claims priority from U.S. Provisional Patent Application Ser. No. 60/554,035, filed Mar. 17, 2004 and is to be incorporated herein in its entirety including all specification and drawings.

BACKGROUND OF THE INVENTION

1. Field of the Invention

The present invention relates generally to the field of orthotic devices and appliances; more particularly to orthotic devices and appliances useful for restoring movement to connective joints (especially to elbow and knee joints) of a mammalian body (especially a human body); and still more particularly to orthotic devices and appliances used to reverse contractures due to immobility and neurological dysfunction.

2. Background Discussion

My prior U.S. Pat. No. 5,891,068, issued on Apr. 6, 1999 (which is incorporated herein in its entirety by specific reference), defines the term "orthotics" (quoting Webster's New Collegiate Dictionary) as "a branch of mechanical and medical science that deals with the support and bracing of weak or ineffective joints or muscles."

As observed in such prior patent, orthotic devices and appliances (commonly referred to just as "orthotics") have been utilized for many years by physical and occupational therapists, as well as certified orthotic fitters, to assist in the rehabilitation of loss of range of motion (LROM) of patients' joints and associated limbs or adjacent skeletal parts of patients' bodies. Thus, orthotics, as well as splints, have been designed both to maintain and to restore the range of bodily motion due to LROM. Such LROM may, for example, be caused by traumatic injury, joint or limb surgery, and/or contracture due to immobilization caused by neuromuscular disorders (e.g., stoke and closed head injury) and other disease processes that significantly limit a patients ability to use a joint for normal activities of daily living (ADL).

Two fundamentally different types of contractures exist which clinically should have two different treatment protocols. The difference in these two types of contractures is the basis for the clinical techniques and design of the orthotics of the present invention which will be described below.

A first one of these two fundamentally different types of contracture may be defined as a fixed, high resistance of muscle to passive stretch resulting from fibrosis of the muscles and joints, or from disorders of the muscle fiber resulting in LROM, for example, of a patient's arm or leg. In this regard, Webster's Dictionary defines "contracture" as "a permanent shortening (as of muscle, tendon and scar tissue) producing deformity or distortion."

This first type of contracture is usually due to trauma, injury, or surgical intervention affecting the joint, as may be typical of sports injuries and the treatment thereof. As the injured tissue heals, edema, post trauma or surgically affected tissue regeneration and other natural healing processes result in the fusing together of what were, prior to the trauma, separate, pristine connective tissues, that is, the collagen fiber matrix (depicted diagrammatically in FIG. 1A of my prior patent), capable of easily gliding over one another, as is needed for normal joint movement and related muscle elongation.

However, post-trauma, this collagen fiber matrix becomes random and irregular (depicted diagrammatically in FIG. 1B of my prior patent), and neither elongates nor stretches compared to non-traumatized collagen fibers. This fusing-together or adhesion of connective tissue structures (e.g., ligaments, tendons, synovial membrane, fascia and fibrous joint capsules) is the result of the tissues being invaded by developing undifferentiated scar between adjacent tissue, thereby diminishing or preventing the mutual gliding after early healing of the trauma or post-surgical trauma has been accomplished.

Such fusing together of connective tissue is a leading cause of lags (a non-specific indictment of the motor system's failure to move the affected joint through the full available passive range) relating to tendon gliding, depending on their strategic placement in reference to structures crossing the joint. With limited mobility and associated extensor muscle atrophy, combined with the formation of adhesions and scar tissue in the form of a significantly increased number of joined fiber matrix junctions, the muscle fibers become shortened.

The restoration of full range of motion (ROM) where fibrosis of the muscle fiber with scar tissue and adhesions are present requires that the adhesions and scar tissue or fused fiber matrix junctions be "worked through" or broken to restore normal functional elongation or stretch. The term "no pain, no gain" (of increased range of motion) is associated with the process of breaking through joined or fused fiber matrix junctions to restore full elongation of the connective tissue, tendons and muscles associated with the trauma-affected joint.

Heretofore known orthotics are primarily designed to treat this first type of contracture, but have also been used to treat contractures caused by immobility and neurological dysfunction (described below). However, such orthotic devices are not, as far as is known by the present inventor, best suited for such additional purpose.

The second and very different type of contracture results from joint immobility—not joint-related trauma or surgical repair of a joint. Contracture resulting from immobility is simply a shortening and thickening of the connective tissue, tendons and muscles (depicted in FIG. 1C of my prior patent) that restrict the ROM of a joint. In such situations, the muscle fibers still retain their original uniform shape and there are no adhesions or scar tissue or significantly increased joined fiber matrix junctions to break through in order to restore full range of motion.

In contrast to trauma-caused contractures, contractures due to immobility do not need a "no pain, no gain" approach to restoring the normal range of motion, and, in fact, such an approach can actually do more harm than good. As mentioned above, the collagen fibers of a contracture due to immobility are simply shorter and thicker, and will respond to appropriate stretching techniques and motion of the joint to restore LROM. The stretching technique usually used for contractures caused by immobility is Range Of Motion (ROM) Therapy and the use of Low-Load Protracted Stretch/Stress (LLPS) or "extended stretch" static or dynamic orthotic devices.

According to authors Kenneth R. Flowers and Susan L. Michlovitz in their article titled "ASSESSMENT AND MANAGEMENT OF LOSS OF MOTION IN ORTHOPEDIC DYSFUNCTION" (published in Postgraduate Advances in PHYSICAL THERAPY, American Physical Therapy Association, 1988 II–VIII), Total End Range Time (TERT) in conjunction with LLPS is the key to restoring full ROM.

All contractures, whether caused by injury, surgery, or immobility, limit range of motion of the affected joint and make simple activities of daily living, such as eating and self-dressing, more difficult, if not impossible. Moderate to severe contractures can be debilitating, and can leave afflicted individuals bed-bound and unable to care for themselves in the most basic daily living tasks. Even mild contractures due to immobility can progress to severe contractures if proper intervention is not prescribed and implemented so long as the immobility continues.

A principal objective of my current invention is accordingly to provide more clinically effective orthotics that are an alternative to the known types of orthotics currently used to treat contractures caused by immobility and the ROM stretching technique. The main function of my new and more effective orthotic devices is to treat contracture due to immobility—not trauma related to surgery or injury.

The present inventor considers that TERT with Activity Stimulus Strategy (i.e., flexing)—not LLPS—is the key to predisposing tissue to elongation and restoring range of motion, where LROM is due to immobility or neurological dysfunction.

The clinical importance and value of orthotics disclosed in my prior patent are significant in that contractures and other hazards of immobility are one of the ten current highest health care costs in America that are totally preventable. This puts the health risks associated with immobility in the same category as cigarette smoking, alcohol and drug abuse, and automobile accidents in financial impact on American health care costs.

The orthotic devices disclosed in my prior patent provide more effective clinical treatment for LROM due to immobility by increasing the "stimulus of activity" of the affected tissue (connective and muscle fiber) rather than just holding the issue in moderately lengthened position (LLPS or "gradual extension" therapy). According to Brand (1984), "It is better not to use the word stretch for what should be long-term growth. If we want to restore normal length to a tissue that has shortened after disease (or disuse), we need to reverse the process and apply the stimulus of activity, or better, the stimulus of holding the tissue in the moderately lengthened position for a significant time." According to Brand, it will then "grow" or lengthen. Flowers and Michovitz in the before-mentioned article theorize that the joint somehow senses or computes the total stress applied to it in any given direction over a period of time. It then stimulates a proportionate amount of biological activity, leading to a proportionate mount of remodeling of the stressed tissue. The total stress is a product of its intensity, frequency and duration. The crucial elements in this conceptual model are frequency and duration. Total stress equals intensity times frequency times duration.

My previously-disclosed orthotic devices increase the stimulus of activity relative to current orthotic devices which simply hold the limb and joint in an extended position for extended periods. Conceptually, patient outcomes should be more positive based upon an increased stimulus of activity as well as providing moderate stretch for a prolonged period with the new devices. The cycling or repeated extension and contraction of the joint by my previously-disclosed orthotics provides the additional benefits of motion (activity), increased lubrication of the tissues (production of synovial fluid) facilitating movement, and muscle re-education and diminished spasticity where neurological dysfunction is present (stroke, closed head injury, MS, etc.). The level of activity is higher with these devices when high tone, spasticity, or moderate to high contraction reflexes are present in the affected limb and joint. Thus my previously-disclosed devices are uniquely appropriate for contractures due to immobility where neurological dysfunction is present in the affected limb.

My prior patent discloses the use of a spring-type interconnection between upper and lower limb attachment members of a limb-type (arm-type and leg-type) orthotic. Such spring-type interconnections provide a torque to applied arms or legs that opposes muscle forces that cause contracture of the limb. Thus, when a contracted arm or leg is manually stretched to increase ROM, and is released after application of the orthotic to the limb, the limb muscles initially overcome the spring forces of the orthotic causing the limb to contract to or toward the initially contracted position. As the limb muscles then tire or relax, the spring forces (that is, torque) of the orthotic stretch or pull the limb back out to or toward the initially stretched position. The limb muscles then again take over and cause another limb contraction against the orthotic spring forces. As the limb muscles again tire or relax, the spring forces (that is, torque) of the orthotic stretch or pull the limb back out to or toward the initially stretched position. As this alternate limb contracting and stretching cycle is repeated, usually many times, (as depicted in attached FIG. 3) the ROM of the limb is gradually increased to that of the initially stretched position.

Although not specifically disclosed the spring force of the orthotic of my prior patent exhibits a typical spring force that increases in a generally linear manner with spring compression and tension. The present inventor has, however, subsequently discovered that an improvement can be made to my previously-disclosed orthotics.

It is thus a principal objective of the present invention to provide a limb-type orthotic having a spring force that initially increases with spring angle over an initial spring angle range, then peaks over an intermediate spring angle range and finally decreases over a final spring angle range, as depicted in FIGS. 3 and 4 of this application, so as to inhibit potentially injurious muscle spasms in the limb to which the present orthotic is attached.

SUMMARY OF THE INVENTION

BRIEF DESCRIPTION OF THE DRAWINGS

The aforementioned object and advantages of the present invention, as well as additional objects and advantages thereof, will be more fully understood hereinafter as a result of consideration of a detailed description of a preferred embodiment when taken in conjunction with the accompanying drawings in which:

FIG. 8 is a presentation generally similar to FIG. 4, of known data and an associated graph showing a linearly increasing average spring torque vs. degree of brace flexing for a dynamic constant linear spring force of known leg orthotics, and showing on the same graph plots of spasm stretch reflex and resting stretch reflex vs. angle of leg flexing;

FIG. 9 is a presentation corresponding to FIG. 8, of known data and an associated graph showing a linearly increasing average spring torque vs. degree of brace flexing for a dynamic constant linear spring force of known arm orthotics, and showing on the same graph plots of spasm stretch reflex and resting stretch reflex vs. angle of arm flexing;

FIG. 10 is a side view of the arm orthotic shown in FIG. 2, showing the arm orthotic in an unflexed condition at representative angle $\alpha_4$ of FIG. 1 (this FIG. corresponds generally to FIG. 5 of my prior patent);

FIG. 11 is a cross sectional drawing taken along line 11—11 of FIG. 10, showing the opposing spring assemblies of the arm orthotic in their unstressed condition (this FIG. corresponds generally to FIG. 6 of my prior patent);

FIG. 12 is a side view of the arm orthotic of FIG. 3 and corresponding to FIG. 10, showing the orthotic in a flexed condition, as by being flexed from representative angle $\alpha_4$ to representative angle $\alpha_3$, and showing central hinged regions the representative first spring assembly in a twisted-out torsion condition (this FIG. corresponds generally to FIG. 7 of my prior patent);

FIG. 13 is a cross sectional drawing taken along line 13—13 of FIG. 12, showing the opposing spring assemblies of the arm orthotic in their twisted-out torsion condition, in which the spring assemblies are twisted out in the direction of arrows B (this FIG. corresponds generally to FIG. 8 of my prior patent);

FIG. 16 is a perspective drawing of the spring assembly lower side bar piece, showing the construction thereof, including the dog-leg shape thereof and the upwardly-extending ribs;

FIG. 17 is a partial perspective drawing of the spring assembly upper side bar piece, showing the hinge region thereof, other regions of the upper side bar piece being identical to those of the lower side bar piece;

FIG. 25 is a drawing corresponding to FIG. 23 showing the representative one of the opposing pair of variation torsion spring assemblies, showing the variation leg orthotic attached to a patient's leg, and further showing a hinge member of the spring assembly configured for a representative progressive ROM use of the orthotic in which the patient's leg is stretched (by way of example) from a the initial stretch angle of 15 degrees to a subsequent stretch angle of 30 degrees for increasing ROM of the leg after the leg can be maintained by the patient at 15 degrees;

FIG. 26 is an enlarged side view of the torsion spring hinge member of FIG. 25 showing the manner in which the pins are installed in the hinge region to provide the representative progressive use of the orthotic in which the patient's leg is stretched to from the flexed angle of 15 degrees to 30 degrees for increasing ROM of the leg after the leg can be maintained by the patient at 15 degrees;

Figure 22:
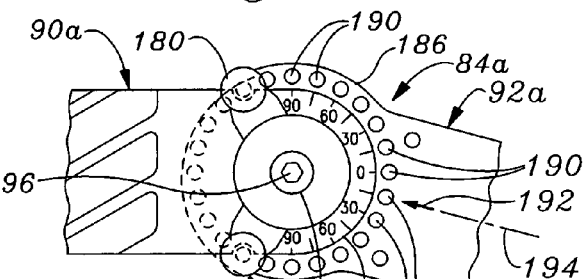
FIG. 22 is an enlarged side view of the torsion spring hinge member of FIG. 21, showing the manner in which the pins are installed in the hinge region to provide the static 15 degree flexure of the patient's leg.
Figure 21:
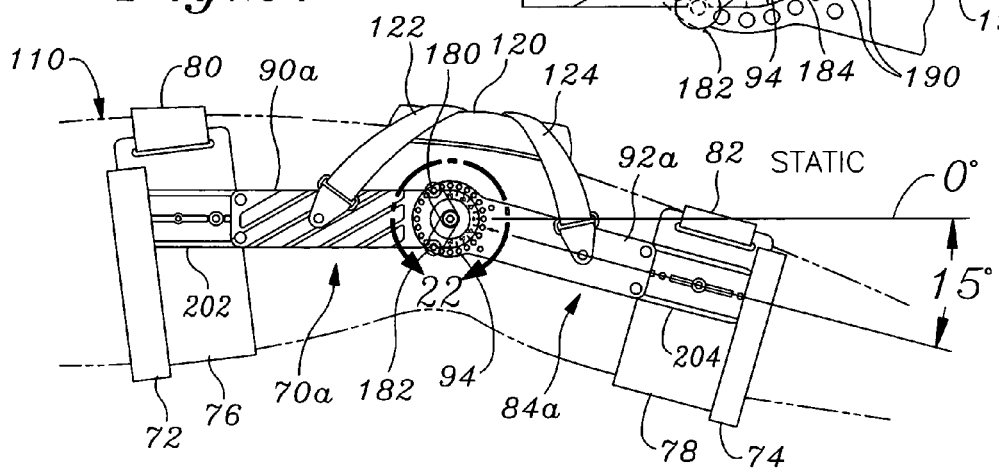
FIG. 21 is a side view of a variation leg orthotic in accordance with the present invention, showing a representative one of the opposing pair of variation torsion spring assemblies, and showing the variation leg orthotic attached to a patient's leg, and further showing a hinge member of the spring assembly configured for a representative static use of the orthotic in which the patient's leg is held (by way of example) immobile at an angle of 15 degrees.
Figure 23:
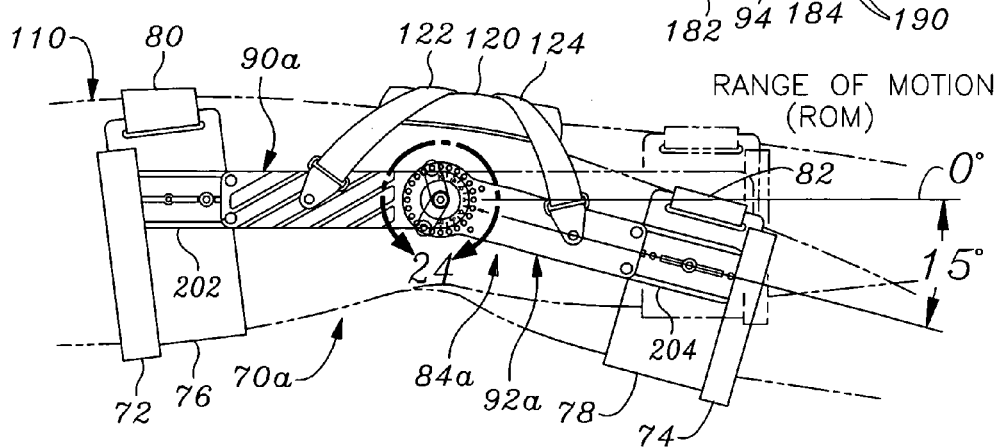
FIG. 23 corresponds generally to FIG. 21 showing the representative one of the opposing pair of variation torsion spring assemblies, showing the variation leg orthotic attached to a patient's leg, and further showing the manner in which the orthotic device is configured to provide a representative Range Of Motion (ROM) use of the orthotic in which the patient's leg is stretched (by way of example) from a straight angle $\alpha_0$ to a slightly flexed angle of 15 degrees for increasing ROM of the leg.
Figure 28A:
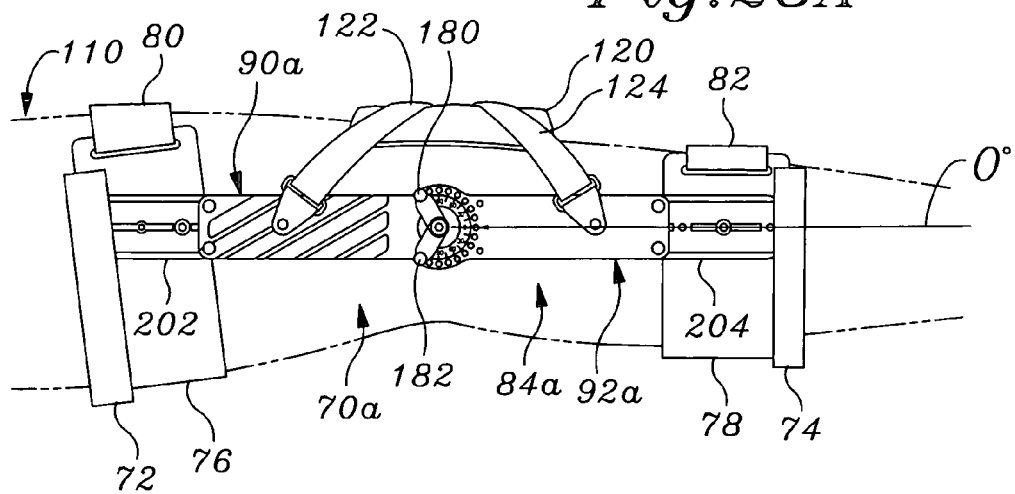
Figure 28B:
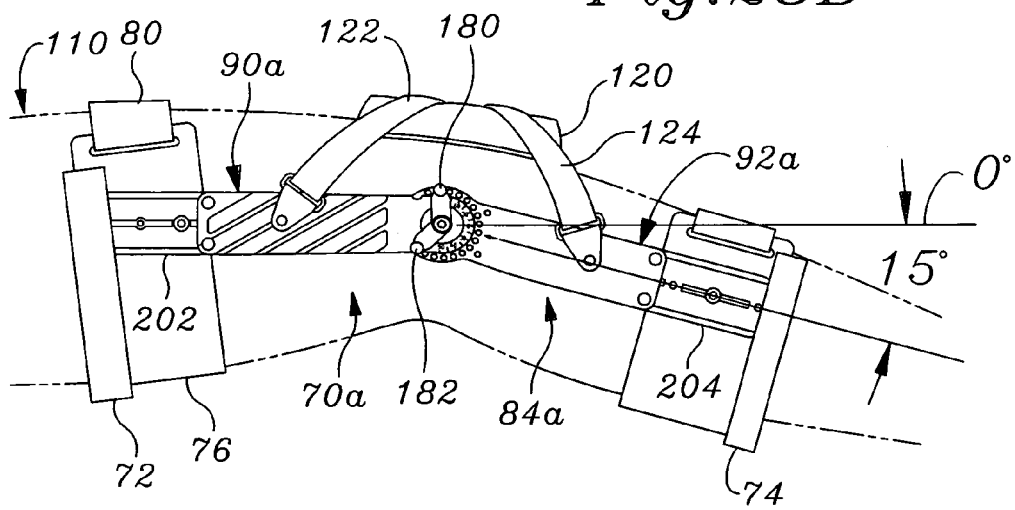
Figure 28C:
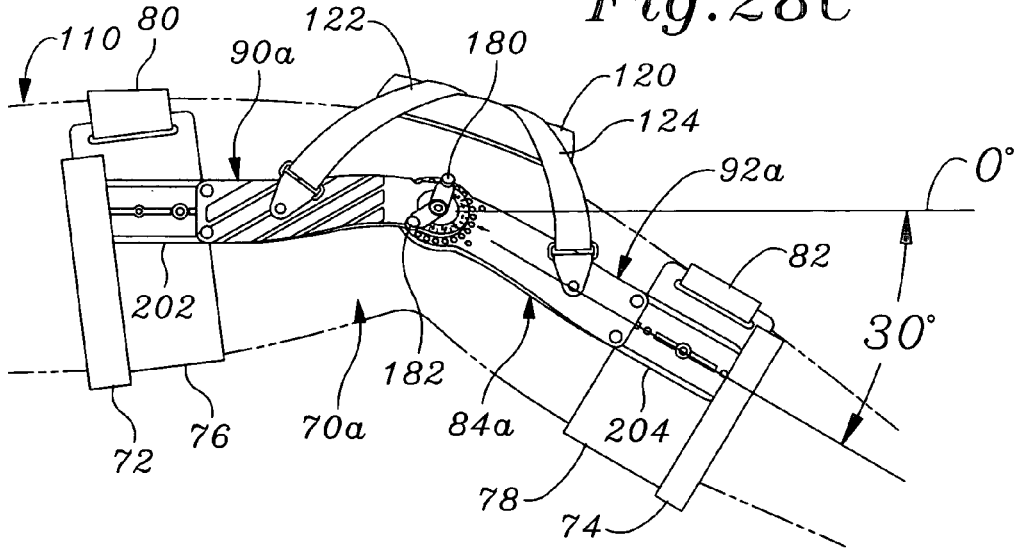
Figure 28D:
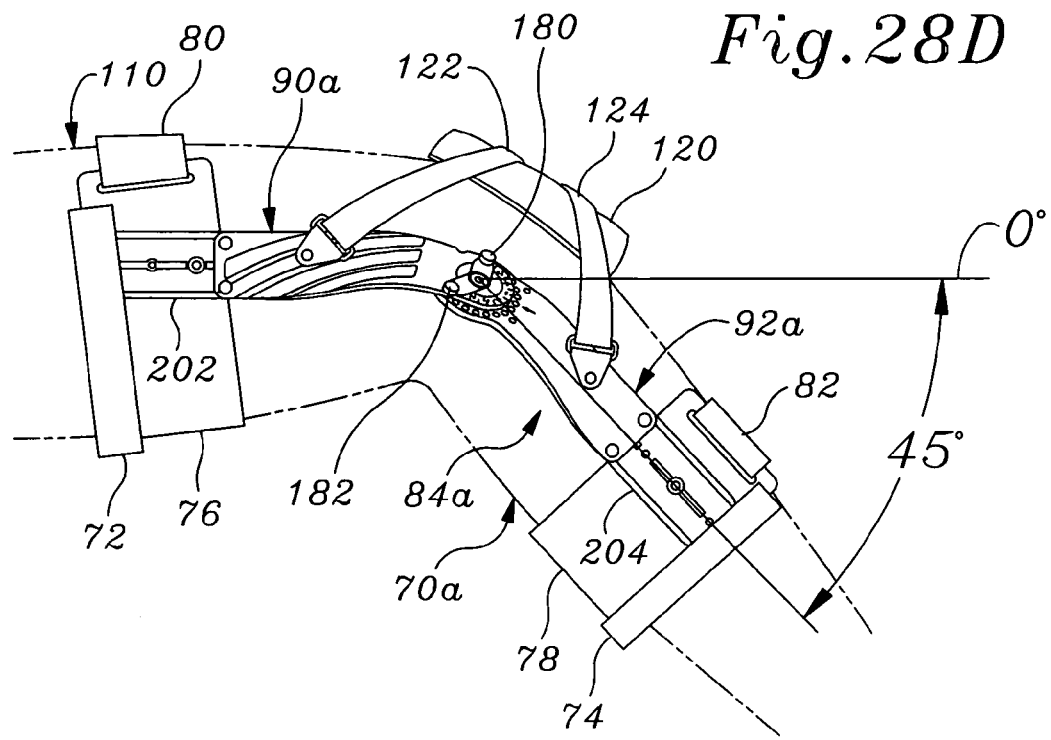
Figure 28E:
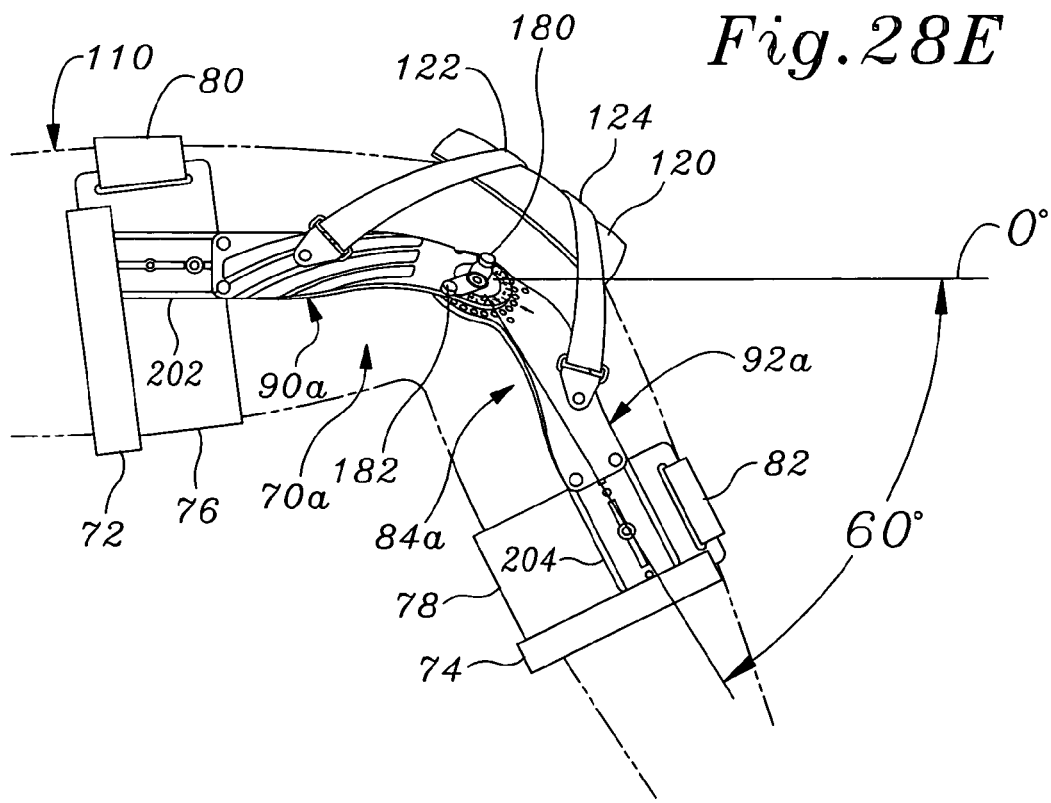
Figure 32A:
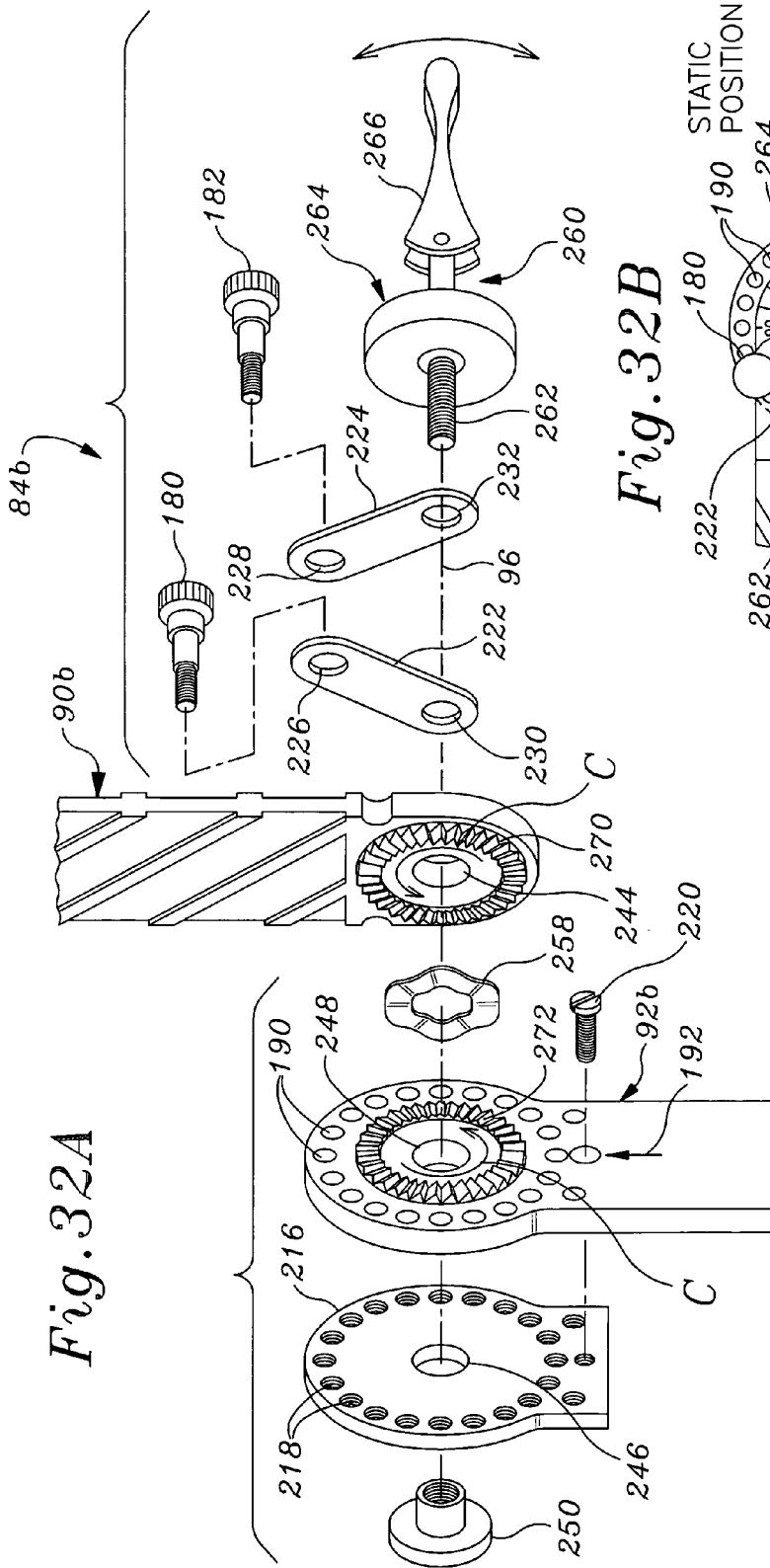
Figure 32B:
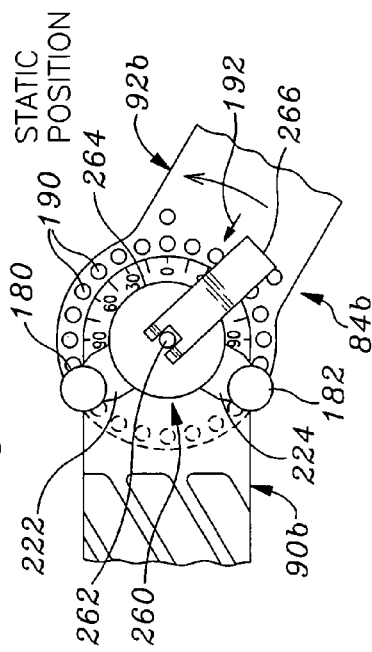
Figure 39:
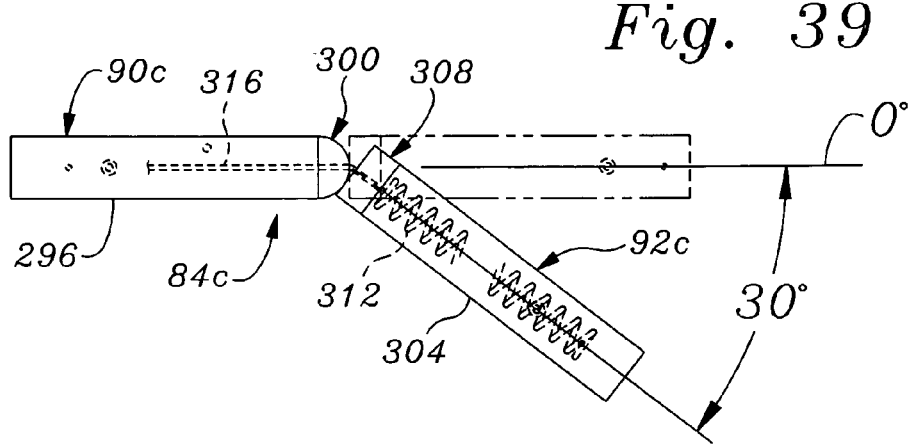
Figure 40:
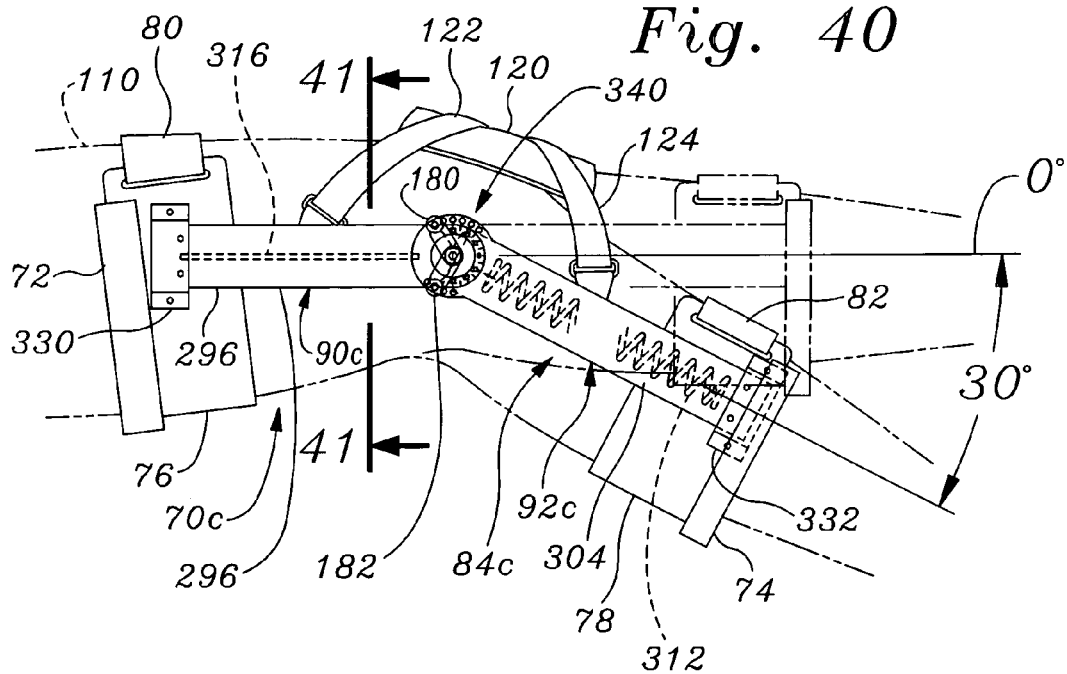
Figure 41:
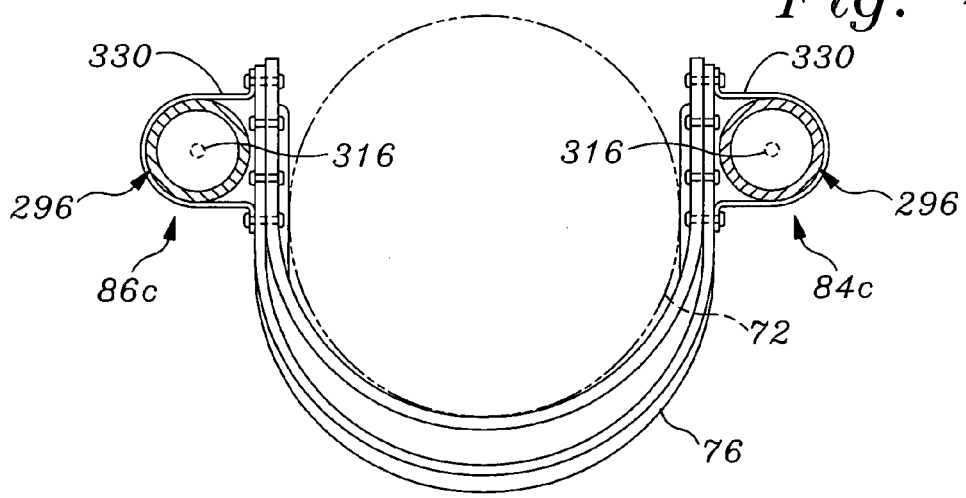
Figure 42A:
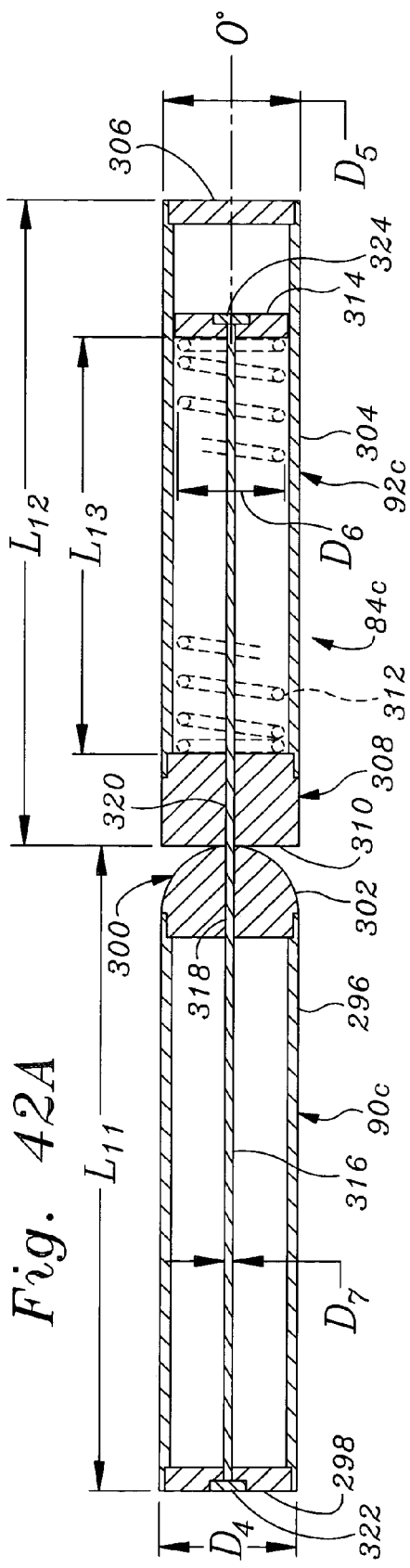
Figure 42B:
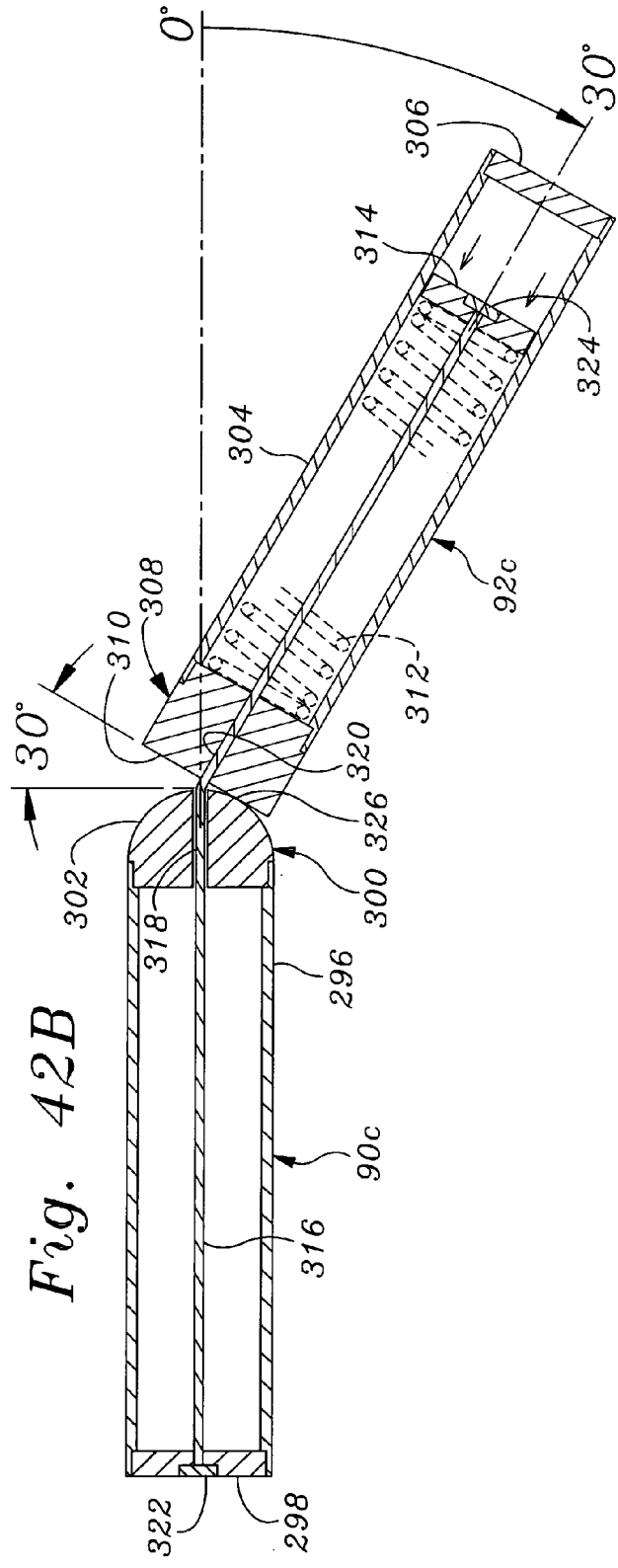

FIG. 27 is a drawing corresponding to FIG. 23 showing the representative one of the opposing pair of variation torsion spring assemblies, showing the variation leg orthotic attached to a patient's leg, and further showing a hinge member of the spring assembly configured for a free motion (within a set plane) use of the orthotic in which the patient's leg is permitted to flex freely between a straight angle, $\alpha_0$, and a large angle, $\beta$ to permit the free exercise of the patient's leg;

FIG. 28A is a side view corresponding to FIG. 21, showing the patient's leg held by the orthotic in the static, straight angle, $\alpha_0$, position; FIG. 28B is a side view corresponding to FIG. 23, showing the patient's leg stretched to the 15 degree ROM position; FIG. 28C is a side view corresponding to FIG. 25, showing the patient's leg contracted from the 15 degree ROM position to the 30 degree position thereby causing the representative interconnecting spring assembly to be slightly bowed out to provide a torque in a manner countering the contracting force; 28D is a side view corresponding to FIG. 28C, showing the patient's leg further contracted to the 45 degree position thereby causing the representative interconnecting spring assembly to be more bowed out to provide a greater torque in a manner countering the contracting force; and FIG. 28E is a side view corresponding to FIG. 28D, showing the patient's leg further contracted to the 60 degree position thereby causing the representative interconnecting spring assembly to be still more bowed out to provide a still greater torque in a manner countering the contracting force;

FIG. 29 is a plan view of the variation orthotic device of FIGS. 21 and 28A, showing the two opposing side spring assemblies in their unstressed, zero torsion condition;

FIG. 30 is a plan view of the variation orthotic device of FIGS. 28E, showing the two opposing side spring assemblies in their bowed-out stressed condition providing a contracture-countering tension;

FIG. 31A is an exploded perspective drawing showing hinge regions of the upper and lower middle side bar pieces, components of the hinge member and the two hinge locking pins; and FIG. 31B is a side view of the assembled hinge member showing the two locking pins installed in locations providing for a 30 degree static position of the associated variation orthotic device;

FIG. 32A is an exploded perspective drawing showing hinge regions of the upper and lower middle side bar pieces, components of a ratcheting version of the hinge member and the two hinge locking pins; and FIG. 32B is a side view of the assembled hinge member showing the two locking pins installed in locations providing for a 30 degree static position of the associated variation orthotic device with the hinge ratcheting lever positioned for engagement of the hinge ratcheting elements;

FIG. 33 is a side view on a representative one of the variation upper middle side bar pieces of the variation spring assemblies, showing features of its construction;

FIG. 34 is a plan view of the upper middle side bar piece of FIG. 33 showing features of its construction, including a plurality of angled ribs and angular markings at an arcuate end thereof;

FIG. 35 is a side view on a representative one of the variation lower middle side bar pieces of the variation spring assemblies, showing features of its construction;

FIG. 36 is a plan view of the upper middle side bar piece of FIG. 35 showing features of its construction, including a circle of locking pin receiving holes at an arcuate end thereof;

FIG. 37 is a transverse cross sectional drawing looking along line 37—37 of FIG. 34, showing other features of the upper middle side bar piece;

FIG. 38 is a transverse cross sectional drawing looking along line 38—38 of FIG. 36, showing a recessed lower surface region of the lower middle side bar piece;

FIG. 39 is a side view of a second variation orthotic device side spring assembly, showing a variation lower middle side member having an internal tension spring, and showing the lower middle side member inclined at an angle relative to a cable-connected upper middle side member;

FIG. 40 is a side view of a second variation leg orthotic device, corresponding generally to FIG. 21, showing the second variation device attached to a patient's leg and showing the hinge member set for a static leg angle of 30 degree, corresponding generally to FIG. 22;

FIG. 41 is a transverse cross sectional drawing looking along line 41—41 of FIG. 40, showing features of the upper middle side member, and showing a cable extending therethrough;

FIG. 42A is a longitudinal cross sectional drawing of the second variation orthotic device spring assembly of FIG. 39, in an in-line, zero angle condition, showing a coiled tension spring installed inside the lower middle side member and a connecting cable installed through the inside of the upper middle side member; and FIG. 42B is a longitudinal cross sectional drawing of the second variation orthotic device spring assembly of FIG. 42A, in the angled condition of FIGS. 39 and 40.

In the various FIGS. identical elements and features are given the same reference numbers and corresponding elements and features for variation orthotic devices are given the original reference numbers followed by an "a" or "b" and so forth as appropriate.

DESCRIPTION OF THE PREFERRED EMBODIMENT

Figure 1:
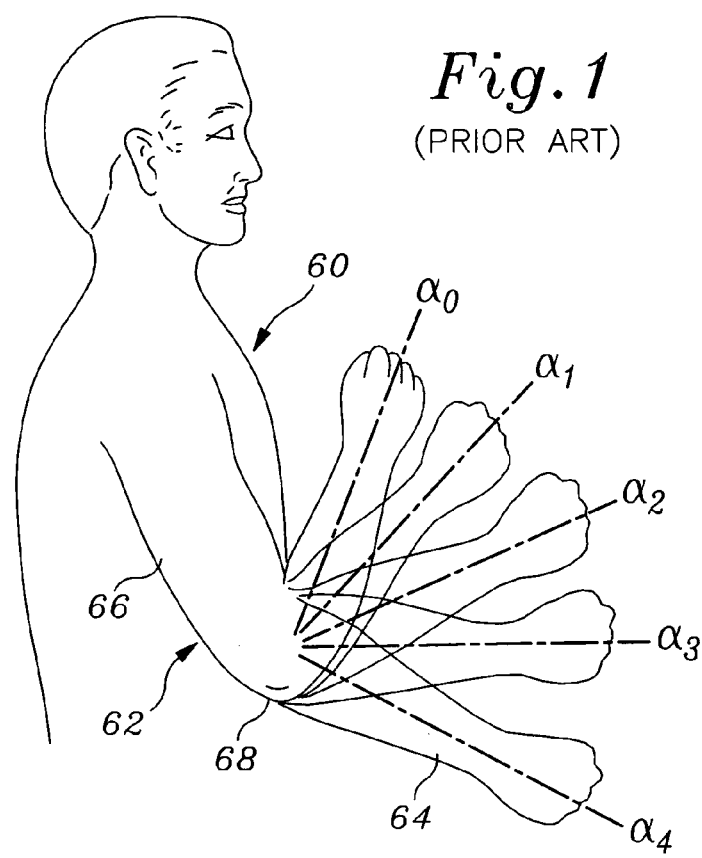
FIG. 1 is a prior art pictorial drawing of an individual's upper torso, showing increased range of motion steps of an individual's arm from the angles $\alpha_0$ through $\alpha_4$ (and is a copy of FIG. 2 of my prior patent)
Figure 2:
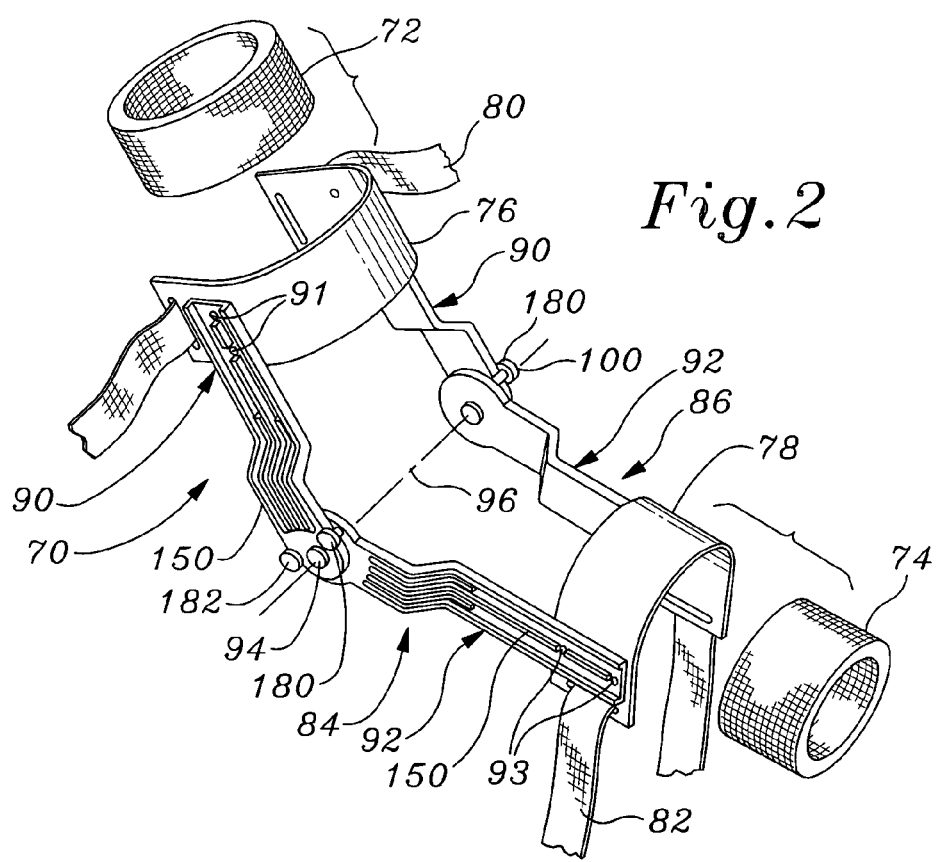
FIG. 2 is a perspective drawing of an arm-type orthotic device in accordance with the present invention, showing upper and lower arm attachment members with associated upper and lower arm cuffs, and showing first and second opposing spring assemblies between the upper and lower arm attachment members (this FIG. corresponds generally to FIG. 4 of my prior patent.

Depicted in FIG. 1, which corresponds to FIG. 2 of my above-referenced prior patent (except for reference numbers differences) is an individual 60 whose limb (i.e., arm) 62 is shown at various angles $\alpha_0$ through $\alpha_4$, of a lower arm region (i.e., lower arm or forearm) 64 relative to an upper limb region (i.e., upper arm) 66, limb joint (i.e., elbow) 68, which represent the stepwise restoration of substantially the full Range Of Motion (ROM) of the limb.

FIG. 2 illustrates a typical upper limb-type orthotic device 70, in accordance with the present invention, configured, as described below, for attachment to respective lower and upper limb regions 64 and 66 about joint 68 of individual's limb 62 for establishing full ROM thereof.

Shown comprising orthotic device 70 are respective upper and lower padded cuffs 72 and 74 which fit around upper and lower limb regions 64 and 66 respectively of limb 62, and associated respective upper and lower, substantially rigid, U-shaped limb attachment members 76 and 78 which fit over cuffs 72 and 74, respectively. Attachment straps 80 and 82 are attached to respective attachment members 72 and 74.

Included in orthotic device 70 are identical first and second spring assemblies 84 and 86. Comprising first spring assembly 84 is an upper side bar piece 90, an upper end of which is connected, as by a pair of rivets 91 to upper limb attachment member 76, and a lower side bar piece 92, a lower end of which is connected by a rivet 93 to lower limb attachment member 78. A lower end of upper side bar piece 90 and an upper end of lower side bar piece 92 are pivotally connected together so as to form a hinge 94 located on a transverse hinge line 96.

In a like manner, second spring assembly 86 comprises upper side bar piece 90, an upper end of which is connected to upper limb attachment member 76, and a lower side bar piece 92, a lower end of which is connected to lower limb attachment member 78. A lower end of upper side bar piece 90 and an upper end of lower side bar piece 92 are pivotally connected together so as to form a hinge 100 on hinge line 96.

As above described, orthotic device 70 is symmetrical except for the settings of hinges 94 and 100.

Figure 3:
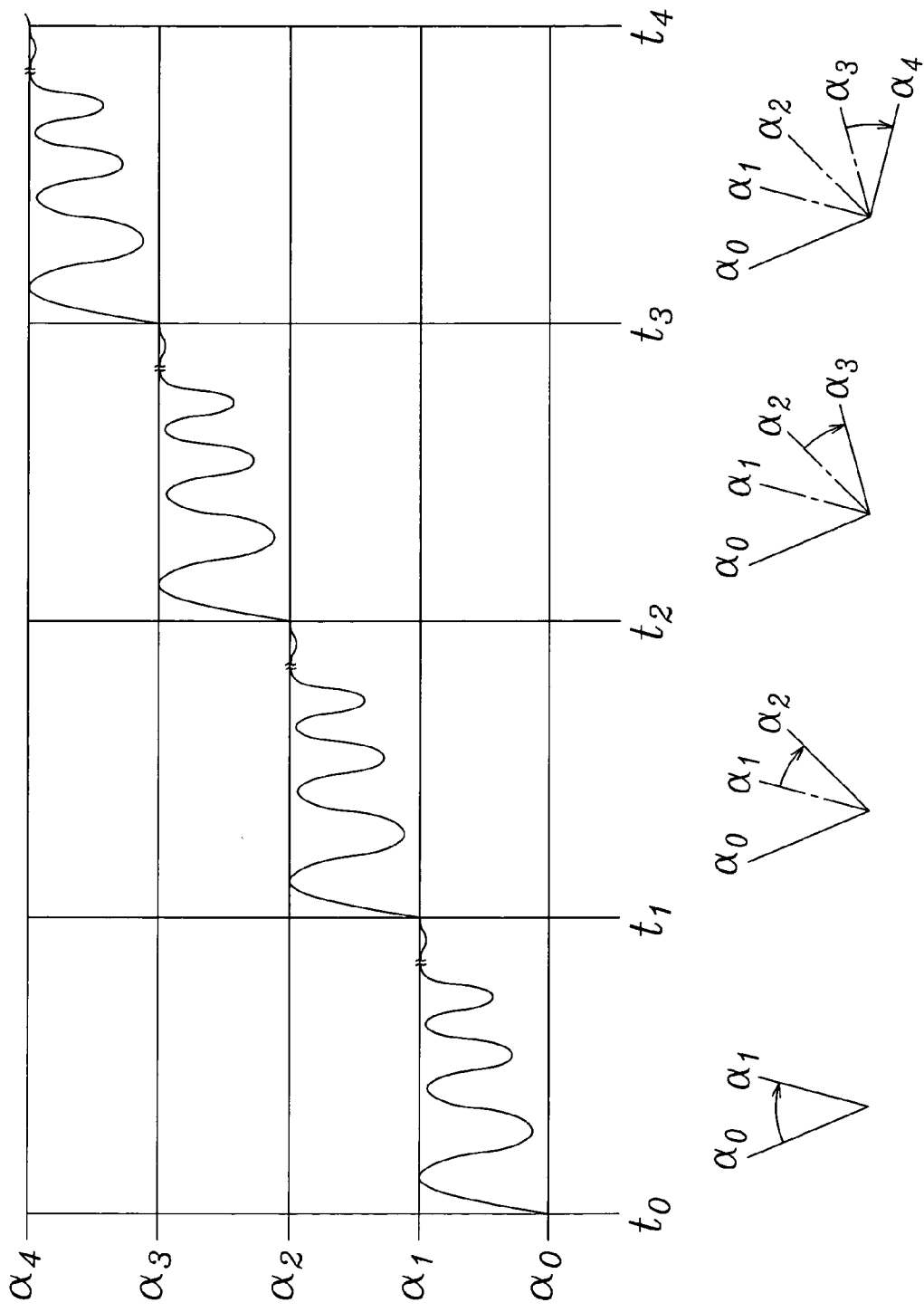
FIG. 3 is prior art diagram showing a representative step-wise increase of range of motions $\alpha_0$, through $\alpha_4$ of FIG. 1, plotted against time intervals $t_0$ through $t_4$ as achieved by use of the orthotic device of FIG. 2 (and is a copy of FIG. 3 of my prior patent)

FIG. 3, which directly corresponds to FIG. 3 of my prior patent depicts the step-wise progression of ROM through angles $\alpha_0$ through $\alpha_0$ of limb 62 shown in FIG. 1 plotter against associated time $t_0$ through $t_4$. A number of repetitive limb extension and retraction cycles are shown for each time interval, $t_0$–$t_1$, $t_1$–$t_2$, $t_2$–$t_3$ and $t_3$–$t_4$, to achieve each successive incremental increase of ROM.

Figure 4:
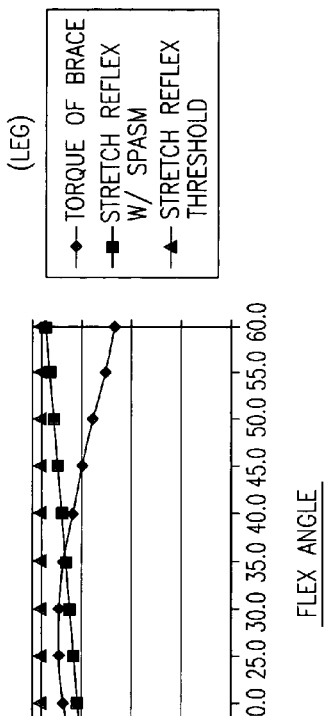
FIG. 4 is a presentation generally similar to subsequent FIGS. 6 and 8, of data and an associated graph showing an increasing and then decreasing spring torque vs. degree of orthotic flexing at a medium-sized knee for a dynamic non-linear negative spring force of a leg orthotic in accordance with the present orthotic invention, and showing on the same graph plots of spasm stretch reflex and resting stretch reflex vs. angle of leg flexing.

Shown in FIG. 4 are data relating to each incremental degree of leg-type orthotic (brace) extension for the "Dynamic of Non-Linear Negative of the Leg" in accordance with the leg orthotic of the present invention for a medium-sized leg. The data includes torque in inch-pounds vs. flex angle for stretch reflex threshold for a medium-sized leg and theoretical leg stretch reflex with spasm. This data is plotted on a graph which shows the constant nature of the stretch reflex threshold and the increasing nature of the stretch reflex with spasm with increasing leg angle of flexure. Importantly shown is that the force of the orthotic (brace) increases over about the initial 25 degrees of flexure, remains substantially constant from about 25 degrees to about 30 degrees of orthotic (brace) flexing, and then decreases thereafter.

Figure 5:
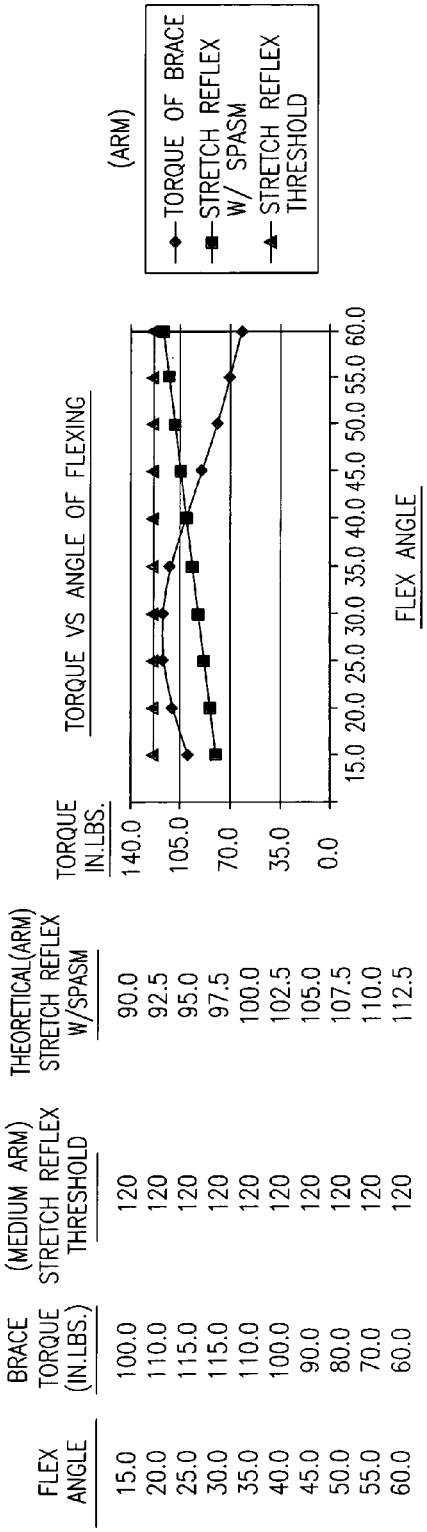
FIG. 5 is a presentation generally corresponding to FIG. 4, of data and an associated graph showing an increasing and then decreasing spring torque vs. degree of orthotic flexing at a medium-sized elbow for a dynamic non-linear negative spring force of an arm orthotic in accordance with the present invention, and showing on the same graph plots of spasm stretch reflex and resting stretch reflex vs. angle of arm flexing.

FIG. 5 corresponds directly to above-described FIG. 4, except that FIG. 5 is for a medium-sized arm instead of for a medium-sized leg. Therefore, the FIG. 4 description is otherwise directly applicable as a description of FIG. 5.

Figure 6:
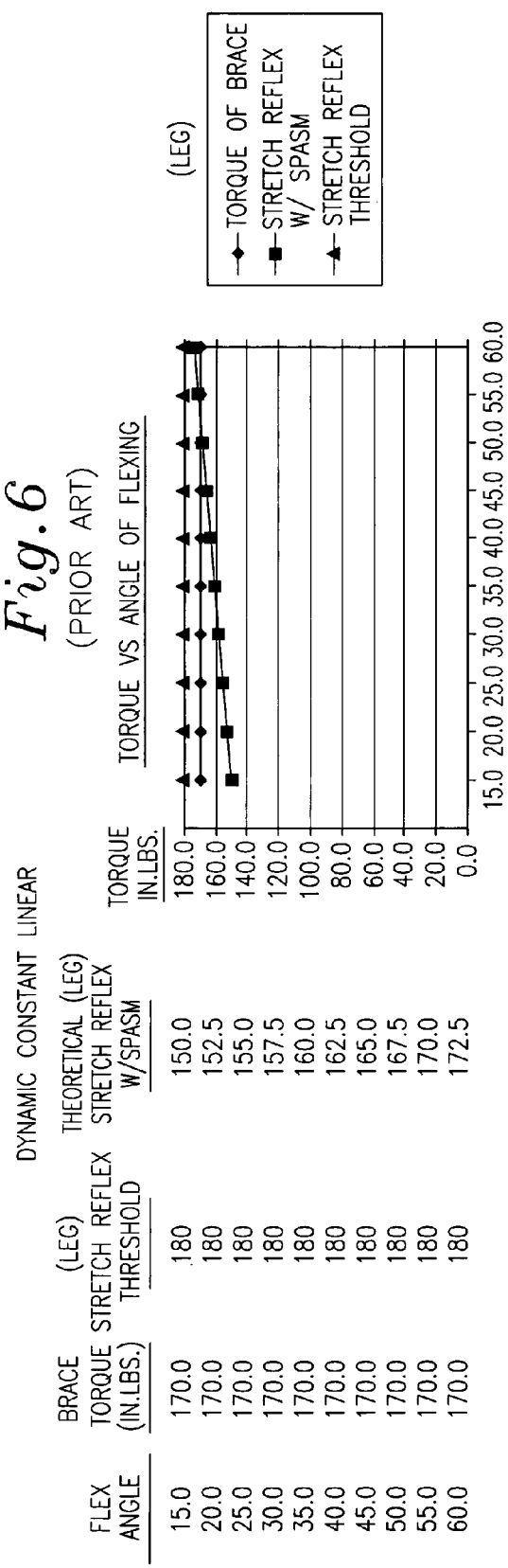
FIG. 6 is a presentation corresponding generally to FIG. 4 of known data and an associated graph showing a curvalinearly increasing average spring torque vs. degree of brace flexing for a dynamic positive linear spring force of known leg orthotics, and showing on the same graph plots of spasm stretch reflex and resting stretch reflex vs. angle of leg flexing.

FIG. 6 corresponds to above-described FIG. 4 except the data and graph are for a conventional "Dynamic Constant Linear" leg-type orthotic. The important difference is that the shown plot of arm torque continuously increases in a slightly curved manner with increasing angle of orthotic (brace) flexing.

Figure 7:
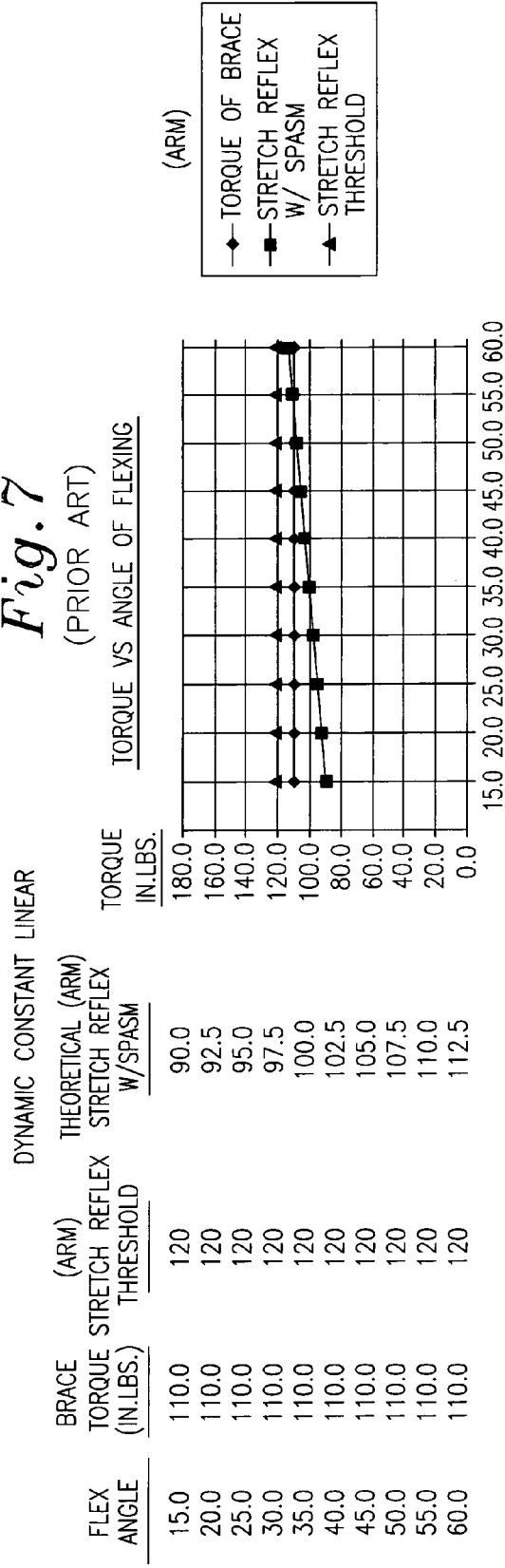
FIG. 7 is a presentation corresponding to FIG. 6, of known data and an associated graph showing a curvalinearly increasing average spring torque vs. degree of brace flexing for a dynamic positive linear spring force of known arm orthotics, and showing on the same graph plots of spasm stretch reflex and resting stretch reflex vs. angle of arm flexing.

FIG. 7 corresponds directly to above-described FIG. 6, except that FIG. 7 is for a medium-sized arm instead of for a medium-sized leg. Therefore, the FIG. 6 description is otherwise directly applicable as a description of FIG. 7.

FIG. 8 corresponds to above-described FIG. 7 except the data and graph are for a conventional "Dynamic Positive Linear" leg-type orthotic. The important difference is that the shown plot of arm torque continuously increases in a straight line manner with increasing angle of orthotic (brace) flexing.

FIG. 9 corresponds directly to above-described FIG. 8, except that FIG. 9 is for a medium-sized arm instead of for a medium-sized leg. Therefore, the FIG. 8 description is otherwise directly applicable as a description of FIG. 9.

Orthotic device 70 of FIG. 2 is shown in FIG. 10 installed onto (i.e., applied to) individual's lower and upper limb (arm) regions 64 and 66, respectively, with shown hinge 94 of spring assembly 84 and hinge 100 of spring assembly 86 (not shown) set, by way of example only, at an angle of $\alpha_4$ degrees. At such $\alpha_4$ angle, orthotic device 70 applies no tension (torque) to arm 62 to which the device is applied.

The FIG. 11 longitudinal cross section of FIG. 10 shows the neutral "dog-leg" configuration of spring assemblies 84 and 86 and that neither of the spring assemblies are flexed.

In FIG. 12, which corresponds generally to FIG. 10, orthotic device 70 is shown installed onto (i.e., applied to) individual's lower and upper limb (arm) regions 64 and 66, respectively, with shown hinge 94 of spring assembly 84 and hinge 100 of spring assembly 86 (not shown) set, by way of example only, flexing from angle $\alpha_4$ depicted in FIG. 10 to a smaller angle $\alpha_3$. As a consequence of such device flexing through an angular increment equal to $\alpha_4$ minus $\alpha_3$, spring assemblies 84 and 86 are twisted out (in the direction of Arrows "A" (FIG. 13) to apply tension (torque) in accordance with FIG. 5, to arm 62 in a manner countering the tension of arm muscles which act to pull the arm to the depicted more contracted $\alpha_3$ angular position.

Figure 14:
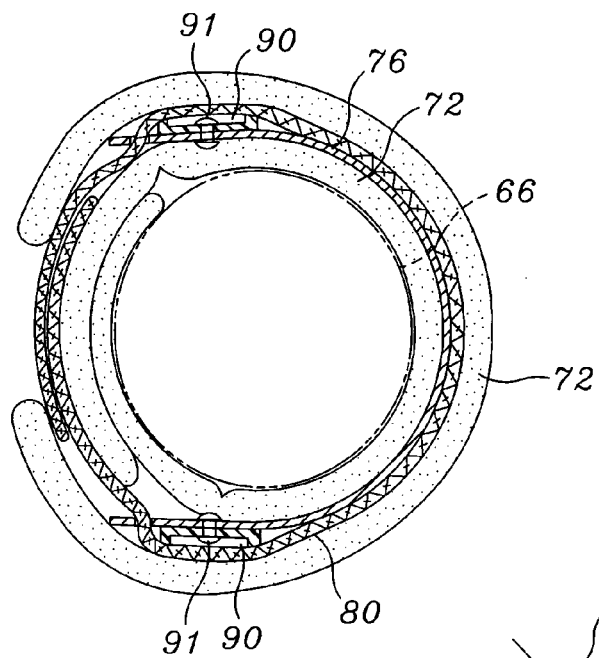
FIG. 14 is a transverse cross sectional drawing looking along line 14—14 of FIG. 10, showing construction of a representative orthotic-to upper arm attachment structure (this FIG. is a copy of FIG. 9 of my prior patent)

The transverse cross sectional drawing of FIG. 14 shows the overlying configuration of representative cuff 72 and U-shaped attachment member 76 depicted in FIG. 10.

Figure 15:
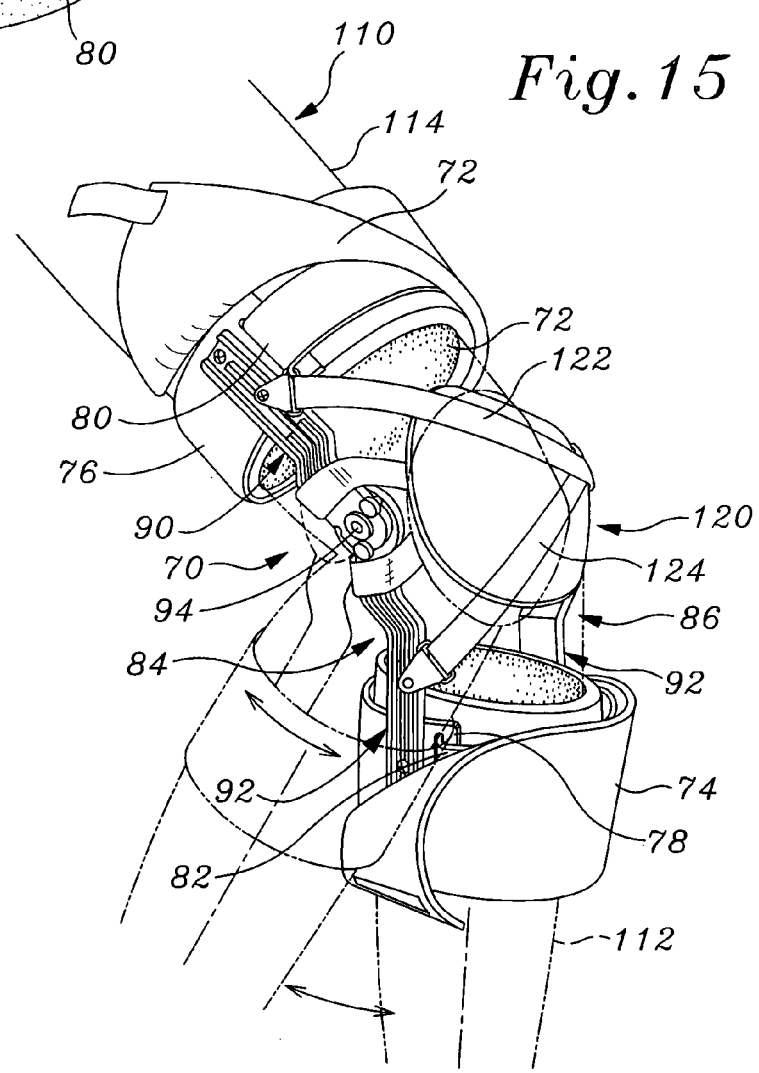
FIG. 15 is a perspective drawing of a leg orthotic in accordance with the present invention, showing the various component thereof and showing attachment thereof to a patient's leg (this FIG. corresponds generally to FIG. 12 of my prior patent)

FIG. 15 depicts a leg-sized orthotic device 70 applied to respective lower and upper regions 112 and 114 of an individual's lower limb (leg) 110. Other that being of a larger (leg vs. arm) size, device 70 for the lower limb is the same as described above for upper limb (arm), having the torsion (torque) characteristics depicted in FIG. 4 for a leg-type orthotic device.

Shown in FIG. 15 covering orthotic device 70 and particularly required for applying the device to lower limb (leg) 110 is a cap-shaped joint (knee) restraining pad 120 that is applied to the lower limb joint (knee joint) (not identified) and held tightly in place by respective first and second straps 122 and 124 that extend cross-wise over pad 120 and are attached to spring assemblies 84 and 86. Pad 120 is further secured by a secondary pad 128 having an attached strap 130 that extends around joint (knee) 132.

As shown in perspective in FIG. 16, lower side bar piece 92 of representative spring assembly 84 is formed having a hinge region 140, with an outside diameter, $D_1$, of about 1.750 inches. Formed centrally in hinge region 140 is a hinge hole 141 having a diameter, $D_2$, that is about 0.188 inch. Extending in a common plane from hinge region 140 is a region 142 having a length, $L_1$, from hinge axis 96, that is about 1.750 inches. A dog-leg region 144 that is angled downwardly from region 142 at about 45 degrees extends from region 142 for a length, $L_2$ from hinge axis 96 that is about 3.188 inches. Dog-leg region 144 has a step=down height, H1, that is about 0.375 inch.

Lower side bar piece 92 is formed having five equally spaced apart longitudinal upstanding ribs 150 that extend for a length, $L_3$, starting at a radius, $R_1$, from hinge line 96 and extending from regions 142–146. Length, $L_3$, may be about 3.188 inches, and radius, $R_1$, may be about 1.188 inches. Thereafter, region 146, which extends the remainder of a total length, $L_4$, of lower side bar piece 92 from hinge axis 96, which may be about 7.750 inches, is formed having three, equally spaced apart ribs 150 which are continuations of the center and side ones of the five ribs 150 of regions 142 and 144.

FIG. 17 is a partial perspective drawing of upper side bar piece 90 of representative spring assembly 84, depicting a hinge region 160, having an outside tip radius $R_2$ of about 0.688 inch, with a hinge hole 161 of diameter, $D_2$, and portions of an adjacent region 162. Otherwise, upper side bar piece 90 is substantially identical to above-described lower side bar piece 92.

Figure 18:
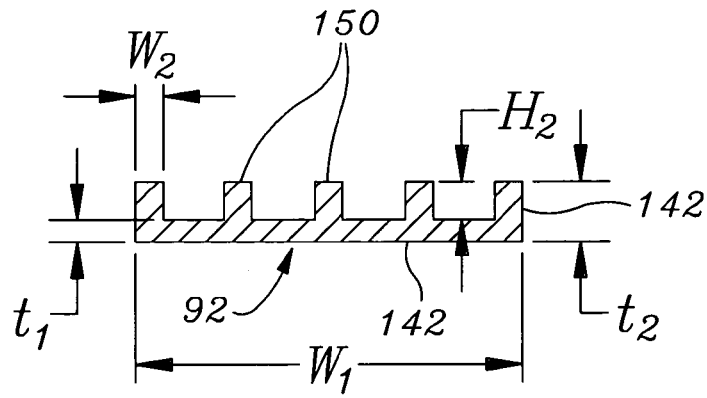
FIG. 18 is a transverse cross sectional drawing looking along line 18—18 of FIG. 16, showing details of an upper region of the lower side bar piece having five, equally spaced apart longitudinal ribs.

As shown in the transverse cross sectional FIG. 18, each of the five ribs 150 are formed having a width, $W_2$, that is about 0.125 inch, and have a height, $H_2$, above a base region, 170, that is about 0.156 inch. A total thickness, $t_2$, of region 140 (as well as regions 142–146) is about 0.250 inch. Base 170 has width, $W_1$ and has a thickness, $t_1$ that is about 0.094 inch. The foregoing dimensions associated with FIG. 18 provide a cross sectional area, $A_1$, of regions 142 and 144 that is about 0.227 square inches.

Figure 19:
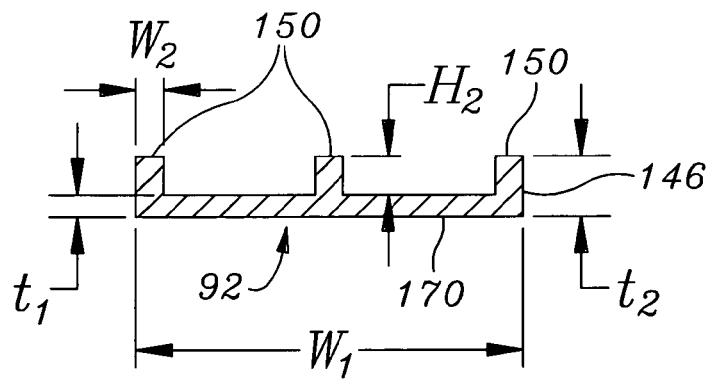
FIG. 19 is a transverse cross sectional drawing looking along line 19—19 of FIG. 16, showing details of a lower region of the lower side bar piece having three, equally spaced apart longitudinal ribs.

As shown in the transverse cross sectional FIG. 19, each of the three ribs 150 are formed having above-described width, $W_2$, and height, $H_2$, above base region 170. Base 170 has width, $W_1$ and thickness, $t_1$. The foregoing dimensions associated with FIG. 19 provide a cross sectional area, $A_2$, of region 146 that is about 0.188 square inches.

Figure 20:
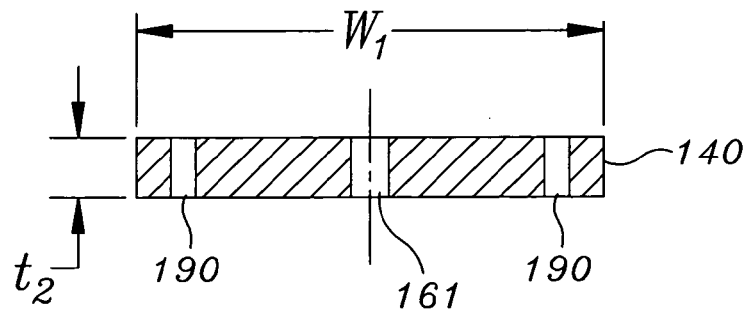
FIG. 20 is a transverse cross sectional drawing looking along line 20—20 of FIG. 16, showing details of a hinge region of the lower side bar piece having no longitudinal ribs.

As shown in the transverse cross sectional FIG. 20, hinge region 140 has above-disclosed width, $W_1$, with hinge hole of diameter, $D_2$, and thickness, $t_2$, with two 0.125 inch diameter holes 190 that provides a total cross sectional area, $A_3$, of the hinge region of about 0.234 square inches. Region 160 of upper side bar piece, without holes 190 (FIG. 17) has a corresponding cross sectional area, $A_4$, of about 0.297 square inch.

The present inventor points out that the above dimensions and cross sectional areas of lower and upper side bar pieces 92 and 90 are for an orthotic device 70 constructed for attachment to an average sized adult leg 110, and with the side bar pieces constructed from injection molded, radiation sterilizable polypropylene copolymer having a modulus of flexure of 1140, the torsion vs. angle of device (brace) flexing characteristic curve shown in FIG. 4 is achieved. These dimensions and associated cross sectional areas can, by those skilled in the art without undue experimentation, be scaled up for orthotic devices for attachment to larger legs 110 and scaled down for orthotic devices for attachment to smaller legs and for arms 62.

Shown in FIGS. 21–31 is a first variation orthotic device 70a which is shown, by way of specific example applied to patient's leg 110, and which has the same torque vs. flex angle characteristics depicted in FIG. 4 for above-described orthotic device 70. However, orthotic device 70a comprises in spite of employing a variation first spring assembly 84a and a second spring assembly 86a, as described below.

A significant feature of orthotic device 70a is that the pivotal (hinged) connection between upper and lower middle side bar pieces 90a and 92 are configurable (that is, can be set) for providing three modes of orthotic device 70a operation. These three modes of operation are: static, Range Of Motion (ROM), and free motion within a set plane—as more particularly described below.

Shown in FIG. 21 comprising orthotic device 70a is a representative first spring assembly 84a, which includes respective upper and lower middle side bar pieces 90a and 92a connected together at hinge point 94, U-shaped limb (leg) attachment members 76 and 78, respectively, to which respective middle side bar pieces 90a and 92a are attached and which are applied to limb (leg) 110 over padded cuffs 72 and 74, respectively. Included is joint (knee) pad 120 which is retained to limb (leg) 110 by straps 122 and 124.

Shown in the enlarged drawing of FIG. 22, pins 180 and 182 are positioned to bear against upper middle side bar piece 90a to set a static angle of 15 degrees between upper and lower middle side bar pieces 90a and 92a. To this end, connection end region 184 of upper middle side bar piece 90a is marked in 15 degree angular increments in a semi-circle to both sides of a 90 degree mark. A connection end region 186 of lower middle side bar piece 92a is formed having a circle of pin mounting holes 190 also at 15 degree intervals. An indexing arrow or pointer 192 adjacent the circle of holes 190 is aligned with a longitudinal axis 194 of lower middle side bar piece 92a and points toward the angular marks on upper middle side bar piece 90a.

As shown, lower middle side bar piece 92a is angled relative to upper middle side bar piece 90a so that arrow 192 points to the lower 15 degree mark on the upper middle side bar piece. With pins 180 and 182 located at stop positions relative to upper middle side bar piece 90a, this set a spring assembly 84a at 15 degrees., with the result that limb 110 is held is the static 15 degree position depicted in FIG. 21. Although spring assembly 84a and the corresponding second spring assembly 86a (not shown) hold limb 110 in the static 15 degree position, the spring assemblies can flex to prevent injury to the limb in the event the limb is unintentionally bumped.

Figure 24:
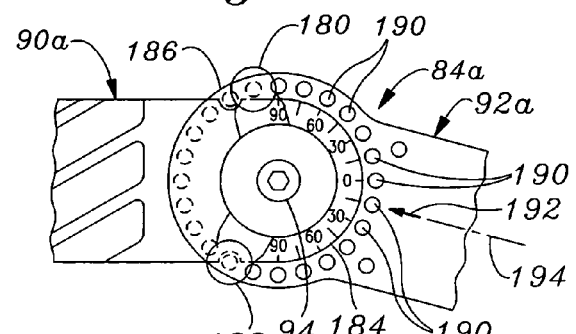
FIG. 24 is an enlarged side view of the torsion spring hinge member of FIG. 23, showing the manner in which the pins are installed in the hinge region to provide the representative ROM use of the orthotic in which the patient's leg is stretched to a slightly flexed angle of 15 degrees for increasing ROM of the leg.

FIGS. 23 and 24 correspond generally to above-described FIGS. 21 and 22, except that pins 180 and 182 are set for 15 degrees ROM (between zero degrees and 15 degrees) with pin 180 installed 15 degrees from stopping against upper middle side bar piece 90a and with pin 182 installed against the upper middle side bar piece.

FIGS. 25 and 26 correspond generally to above-described FIGS. 23 and 24, except that arrow 190 is pointed at 30 degrees and pins 180 and 182 are set for 30 degrees greater ROM (between zero degrees and 30 degrees). Pin 180 is thus installed 30 degrees from stopping against upper middle side bar piece 90a and pin 182 is installed against the upper middle side bar piece.

FIG. 27 correspond generally to above-described FIGS. 23 and 25, except that pins 180 and 182 are both removed from holes 190 so as to enable free motion between upper and lower middle side bar pieces 90a and 92a to thereby enable free movement, within a set plane, exercise of limb 110 through an indeterminate angle, β, which may be between zero degrees (limb 110 out straight) and about 120 degrees.

FIGS. 28A–28E are a series of drawings corresponding generally to above-described FIGS. 21–27, each showing variation orthotic 70a applied to limb (leg) 110 and with representative variation first spring assembly 84a set at zero degrees between upper and lower middle side bar pieces 90a and 92a (FIG. 28A), at 15 degrees (FIG. 28B), at 30 degrees (FIG. 28C), at 45 degrees (FIG. 28D), and at 60 degrees (FIG. 28E).

Variation first spring assembly 84a is depicted with upper and lower middle side bar pieces 90a and 92a increasingly bowed out providing increased restoring torque (that is, muscle contraction force countering) in accordance with FIG. 4, as the angle of limb (leg) flexing is progressively increased from 15 degrees to 60 degrees (FIGS. 28B–28E).

FIG. 29 is a view looking down on variation orthotic device 70a applied to limb (leg) 110, corresponding to the setting of spring assembly 84a depicted in FIGS. 21 and 28A, also showing variation spring assembly 86a. Both variation spring assemblies 84a and 86a are shown in their unflexed state.

FIGS. 29 shows distal end regions of upper and lower middle side bar pieces 90a and 92a connected by spacers 200 to respective upper and lower end side bar pieces 202 and 204, respectively, which are step-down extensions thereof and which attach spring assemblies 84a and 86a to respective limb attachment members 76 and 78. For a medium-sized leg 110, an effective length, $L_5$, of variation spring assembly 84a and 86a between an attachment axis 206 at limb attachment member 76 and hinge axis 96 may be about 7.50 inches and an effective length, $L_6$, of variation spring assembly 84a and 86a between an attachment axis 208 at limb attachment member 78 and hinge axis 96 may be about 7.50 inches. Spacers 200 provide an off-set height, $H_3$, between upper and lower middle side bar pieces 90a and 92a and associated end side bar pieces 202 and 204 which is about 0.750 inch.

In contrast to FIG. 29, FIG. 30, which is also a downward looking view of variation orthotic device 70a, showing both variation spring assemblies 84a and 86a in their flexed state. This flexed state corresponds to the flexed state depicted in FIG. 28E, and shows upper and lower middle side bar pieces 90a and 92a twisted outwardly in the direction of arrows "A", thereby causing hinge-connecting regions thereof to twist inwardly in the direction of arrows "B" to achieve the torque vs. flex angle characteristics of FIG. 4.

FIG. 31A is an exploded perspective drawing of first variation first spring assembly 84a (which is also representative of variation second spring assembly 86a, not shown) forming part of first variation orthotic device 70a (also not shown). FIG. 31A shows those portions of respective upper and lower middle side bar pieces 90a and 92a (which are more particularly described below relative to FIGS. 33–38) adjacent hinge line 96. Shown positioned between upper and lower middle side bar pieces 90a and 92a (which are constructed from plastic as described below) is a rigid metal plate 216 having a circle of threaded holes 218 which match the shown circle of holes 190 in lower middle side bar piece 92a. Plate 216 is attached to lower middle side bar piece 92a by a screw 220.

First and second narrow metal pin-guide plates 222 and 224, respectively, have respective upper holes 226 and 228 for receiving associated pins 180 and 182 and respective lower holes 230 and 232 for receiving an assembly screw 240. Upon assembly of variation spring assembly 84a screw 240 extends through holes 232 and 234, through a washer 242, through holes 244, 246 and 248 in upper middle side bar piece 90a, metal plate and lower middle side bar piece 92a, respectively, and into a nut 250.

FIG. 31B is a side view of hinged regions of upper and lower middle side bar pieces 90a and 92a, showing pins 180 and 182 at a 30 degree static setting of spring assembly 84a, and corresponds generally to FIG. 22.

FIG. 32A is an exploded perspective drawing of a second variation ratcheting-type first spring assembly 84b (which is also representative of a corresponding ratcheting-type second variation second spring assembly 86b, not shown) forming part of first variation, ratcheting-type orthotic device 70b (also not shown). FIG. 32A, which corresponds generally to FIG. 31A, shows those portions of respective ratcheting-type upper and lower middle side bar pieces 90b and 92b (which are identical, except as specifically described below to above-described upper and lower middle side bar pieces 90a and 92a, adjacent hinge line 96. Shown comprising second variation ratcheting-type first spring assembly 84b, are upper and lower middle side bar pieces 90b and 92b (which are constructed from plastic as described below), first and second narrow metal pin-guide plates 222 and 224, pins 180 and 182, rigid metal plate 216 having a circle of threaded holes 218 which match the shown circle of holes 190 in lower middle side bar piece 92b, nut 250, a spring-type washer 258 (for example, a Belville washer) and a toggle-type fastener 260. As shown, plate 216 is disposed between nut 250 and lower middle side bar piece 92b and is attached thereto by screw 220. Spring-type washer 258 is disposed between upper and lower side bar pieces 90b and 92b. Fastener 260 comprises a threaded shaft 262 extending through a thick washer 264, to an unthreaded region of which is pivotally attached a handle 266. Upon assembly of second variation spring assembly 84b, fastener threaded shaft 262 extends pin-guide plate holes 232 and 234, through holes 244 in upper middle side bar piece 90b, through spring-type washer 258, through holes 248 and 246 in lower middle side bar piece 92b and metal plate 216 respectively, and into a nut 250.

The differences between second variation upper and lower middle side bar pieces 90b and 92b and first variation upper and lower middle side bar pieces 90a and 92a is that second variation upper and lower middle side bar pieces 90b and 92b are constructed having respective, mating, circular, one-war ratcheting gear members 270 and 272 around holes 244 and 248 respectively. When engaged, as described below, ratcheting gear members 270 and 272 permit 5 degree incremental of ratcheting between second variation upper and lower middle side bar pieces 90b and 92b in the direction of arrows "C". When fastener handle 266 is in the straight-out position shown in FIG. 32A, spring washer 258 keeps gear members 270 and 272 from engagement with one another. In this condition, second variation first spring assembly 84b (and second spring assembly 86b) function exactly as described above for first variation first spring assembly 84a (and second spring assembly 86a). However, when fastener handle 266 is in the toggled-over condition depicted in FIG. 32B, in addition to functioning exactly as described above for first variation first spring assembly 84a (and second spring assembly 86a), forces applied to second variation first spring assembly 84b (and second spring assembly 86b) enable a 5 degree ratcheting between second variation upper and lower middle side bar pieces 90b and 92b without resetting pins 180 and 182. FIG. 31B is a side view of hinged regions of upper and lower middle side bar pieces 90b and 92b, showing pins 180 and 182 at a 30 degree static setting of spring assembly 84b, and corresponds generally to FIG. 31B.

FIGS. 33–38 show details of first variation upper and lower middle side bar pieces 90a and 92a, which are also applicable to second variation upper and lower middle side bar pieces 90b and 92b (not shown).

FIGS. 33 and 34 are respective side and top plan views of variation upper middle side bar piece 90a having a length, $L_7$, from the center of hole 244 to an opposite end 280 that may be about 4.688 inches, a width $W_2$, that may be about 1.375 inches, and an overall thickness, $t_3$, that may be about 0.625 inch. A pair of hemispheric, pin-stop recesses 282 of about 0.0625 inch radius are formed into opposite sides 284 and 286 of upper middle side bar piece 90a touching an end radius, $R_3$, that is equal to $W_4/2$ or is about 0.688 inch.

Formed at about 30 degrees along a top and bottom 290 and 292 of upper middle side bar piece 90a are five, longitudinally, equally spaced-apart upstanding ribs 294 that have a common width, $W_5$, that is about 0.259 inch.

Ribs 294 extend for a length, $L_8$, from end 280 that may be about 3.418 inches, and have a height, $H_2$, of about 0.0626 inch (FIG. 37). Arcuate end 296 of upper middle side bar piece 90a is marked in 15 degree increments from each side of a central zero mark for enabling angular setting between upper and lower middle side bar pieces 90a and 92a.

FIG. 37 is a transverse cross section of the ribbed region of upper middle side bar piece 90a and shows ribs 294 on both upper and lower sides of such side bar piece having cross sectional widths, $W_6$, that are about 0.312 inch, thereby providing a cross sectional area, $A_5$, of about 0.672 square inch.

A corresponding cross sectional area, $A_6$, taken along hinge line 96 of upper middle side bar piece 90a is about 0.742 square inch.

FIG. 35 is a side view of variation lower middle side bar piece 92a showing a thickness, $t_5$, thereof that may be about 0.250. FIG. 36 is a top plan view of variation lower middle side bar piece 92a showing an elongate region 280 having a width, $W_5$, that may be about 1.625 inches and an enlarged circular end region 282 having a diameter, $D_3$, that may be about 2.125 inches. Formed around circular end region 282 adjacent the edge thereof is a circle of 244 equally spaced pin receiving holes 190. A length, $L_9$, from the center of region 282 to an end 284 of region 280 may be about 4.038 inches.

As shown in FIGS. 36 and 38, an under side region 288 of variation lower middle side bar piece 92a is recessed leaving a surrounding ridge 290 having a thickness, $t_6$, that is about 0.062 inch (that being equal to the depth of recessed region 288). Recessed region 288 has a width, $W_6$, that may be about 1.250 inches and a length, $L_{10}$, that may be about 2.35 inches. This provides an area, $A_7$, of a cross section of variation lower middle side bar piece 92a through recess 288 (FIG. 38) that may be about 0.328 square inch. a corresponding cross sectional area, $A_8$, through the center of region 282 may be about 0.422 square inch.

The present inventor points out that the above dimensions and cross sectional areas of variation lower and upper side bar pieces 90a and 92a are for an orthotic device 70a constructed for attachment to an average sized adult leg 110, and with such middle side bar pieces, as well as upper and lower end side bar pieces 202 and 204 (described above), constructed from injection molded, radiation sterilizable polypropylene copolymer having a modulus of flexure of 1480, the torsion vs. angle of device (brace) flexing characteristic curve shown in FIG. 4 is achieved. These dimensions and associated cross sectional areas can, by those skilled in the art without undue experimentation, be scaled up for orthotic devices for attachment to larger legs 110 and scaled down for orthotic devices for attachment to smaller legs and for various sizes of arms 62.

Shown in FIGS. 39–42 is a third variation first spring assembly 84c that is representative of third variation second spring assembly 86c identified in FIG. 41; both of the spring assemblies comprise third variation orthotic device 70c. Forming third variation first spring assembly 84c are respective third variation upper and lower side bar pieces 90c and 92c. The convention of referring to pieces 90c and 92c as side bars is maintained, for consistency of description, even though such pieces are, in fact, cylindrical pieces and not flat bars.

As shown in FIG. 42a, third variation upper side bar piece 90c comprises a cylindrical tube 296 having a length, $L_{11}$, that may, for a medium-sized leg 110, be about 6.50 inches and having an outside diameter, $D_4$, that may be about 0.75 inch. Tube 296 is closed at one end by a disc-shaped plug 298 and at the other end, adjacent lower side bar piece 92c, by a hemispherical-shaped plug 300 having a hemispherical surface 302.

Tube 296 and plugs 298 and 300 are preferably constructed from a high strength, hard aluminum alloy.

Second variation lower side bar piece 92c comprises a cylindrical tube 304 having a length, $L_{12}$, that may, for a medium-sized leg 110, be about 7.0 inches and having an outside diameter, $D_5$, that may be about 0.938 inch. Tube 304 is closed at one end by a disc-shaped plug 306 and at the other end, adjacent upper side bar piece 90c, by another disc-shaped plug 308 having a flat transverse surface 310.

Tube 304 and plugs 306 and 308 are preferably constructed from a high strength, hard aluminum alloy.

Installed in tube 304 is a compression spring 312 having about 30 coils, with a diameter, $D_6$, of about 0.626 inch and an overall, uncompressed length, $L_{13}$, that may be about 4.0 inches. A disc-shaped piston 314 is installed at the bottom of spring 312. A steel cable 316 having a diameter, D7, that is about 0.094 inch, is installed in tubes 298 and 304, passing through a small central hole 318 in plug 300 and a small central hole 320 in plug 308 and extending longitudinally through spring 312. One end of cable 316 is attached to plug 298 by a fitting 322 and the other end thereof is attached to piston 314 by a fitting 324.

The length of cable 316 is such that spring 312, in its uncompressed state, (FIG. 42A) is closely confined between plug 308 and piston 314 so that any angular flexing between upper and lower side bar pieces 90c and 92c causes compressing of the spring by the cable pulling on the piston (FIG. 42B). Such angular flexing has a hinge point 326 which is the contact point between surface 302 of plug 300 and surface 310 of plug 308, and which changes location as lower side bar piece 92c pivots relative to upper side bar piece 90c. As a result of such variable location of hinge point 326, in conjunction with compression spring 312 and cable 316, provides the torque vs. flexing angle (of spring assemblies 84c and 86c) depicted in FIG. 4.

As shown in FIG. 40, a free end of upper side bar tube 296 is attached to U-shaped leg attachment member 76 by a clamp 330. In a like manner, a free end of lower side bar tube 304 is attached to U-shaped leg attachment member 78 by a clamp 332.

Attached to spring assembly 84c, as well as second spring assembly 86c (not shown in FIG. 40) at the inter-connection point between third variation upper side bar piece 90c and third variation lower side bar piece 92c, and connected thereto is a locking assembly 340 which corresponds directly to FIGS. 22, 24 and 26 which permits the controlling of relative angular flexing between the upper and lower side bar pieces in the manner described above.

Although there is described and illustrated herein an orthotic device and variations thereof, for purposes of illustrating the manner in which the present invention may be used to advantage, it is to be understood that the invention is not limited thereto. Consequently, any and all variations and equivalent arrangements which may occur to those skilled in the applicable art are to be considered to be within the scope and spirit of the invention as set forth in the claims which are appended hereto as part of this application.

What is claimed is:

1. An orthotic device for restoring range of motion to a patient's limb, said orthotic device comprising:
   a. a first device cuff configured for attaching said device to an upper region of said patient's limb above a limb joint;
   b. a second device cuff configured for attaching said device to a lower region of said patients limb below said limb joint;
   c. spring means attached between said first and second cuffs for bending in a manner counteracting muscle contraction of the limb to which the device is attached attempting to bend said limb from an extended position to a more contracted position, said spring means having spring characteristics whereby a counteracting spring force of said spring means increases during an initial flexing of the spring means through a first angle range, then remains peaked during a subsequent flexing of the spring means through a second angle range and finally decreases with a subsequent flexing of the spring means through a third angle range.

2. The orthotic device as claimed in claim 1, wherein said limb is a patient's leg, and wherein said limb joint is a knee joint.

3. The orthotic device as claimed in claim 1, wherein said limb is a patient's leg, and wherein said limb joint is an elbow joint.

4. The orthotic device as claimed in claim 1, wherein said first angle range is between zero degrees and about 25 degrees.

5. The orthotic device as claimed in claim 1, wherein said second angle range is between about 25 degrees and about 30 degrees.

6. The orthotic device as claimed in claim 1, wherein said third angle range is between about 30 degrees and about 60 degrees.

7. The orthotic device as claimed in claim 1, wherein said spring means includes upper and lower spring elements, one end of said upper spring element being attached to said first device cuff and one end of said second spring element being attached to said second device cuff, other ends of the upper and lower spring elements being pivotally interconnected by a hinge element generally aligned with said limb joint.

8. The orthotic device as claimed in claim 7, wherein at least one of said upper and lower spring elements comprise a torsion spring element which twists in a manner providing said counteracting spring force.

9. The orthotic device as claimed in claim 7, wherein at least one of said upper and lower spring elements comprise a tension spring element which stretches in a manner providing said counteracting spring force.

10. The orthotic device as claimed in claim 1, wherein said spring means include first spring means located to one side of said limb joint and second spring means located to an opposite side of said limb joint.

* * * * *